United States Patent [19]
Yoon

[11] Patent Number: 5,584,848
[45] Date of Patent: *Dec. 17, 1996

[54] SAFETY PENETRATING INSTRUMENT WITH PENETRATING MEMBER, SAFETY MEMBER AND CANNULA MOVING DURING PENETRATION AND TRIGGERED SAFETY MEMBER PROTRUSION

[76] Inventor: InBae Yoon, 2101 Highland Ridge Dr., Phoenix, Md. 21131

[ * ] Notice: The term of this patent shall not extend beyond the expiration date of Pat. No. 5,431,635.

[21] Appl. No.: 362,222

[22] Filed: Dec. 23, 1994

Related U.S. Application Data

[63] Continuation-in-part of Ser. No. 83,220, Jun. 24, 1993, Pat. No. 5,431,635, Ser. No. 83,728, Jun. 29, 1993, Pat. No. 5,466,224, and Ser. No. 115,152, Sep. 2, 1993.

[51] Int. Cl.$^6$ ..................................... A61M 5/20
[52] U.S. Cl. ..................... 606/185; 604/165; 604/170
[58] Field of Search ..................... 128/751, 752, 128/753, 754; 604/95, 158, 162, 163, 164, 165, 170, 272, 274, 280, 169; 606/167, 171, 185

[56] References Cited

U.S. PATENT DOCUMENTS

| | | |
|---|---|---|
| 1,087,845 | 2/1914 | Stevens . |
| 1,213,001 | 1/1917 | Philips . |
| 1,248,492 | 12/1917 | Hill . |
| 1,527,291 | 2/1925 | Zorraquin . |
| 2,496,111 | 1/1950 | Turkel . |
| 2,623,521 | 12/1952 | Shaw . |
| 2,630,803 | 3/1953 | Baran . |
| 4,254,762 | 3/1981 | Yoon . |
| 4,345,589 | 8/1982 | Hiltebrandt . |
| 4,535,773 | 8/1985 | Yoon . |
| 4,559,041 | 12/1985 | Razi . |
| 4,601,710 | 7/1986 | Moll . |
| 4,627,841 | 12/1986 | Dorr . |
| 4,654,030 | 3/1987 | Moll et al. . |
| 4,828,547 | 5/1989 | Sahi et al. . |
| 4,869,717 | 9/1989 | Adair . |
| 4,902,280 | 2/1990 | Lander . |
| 4,931,042 | 6/1990 | Holmes et al. . |
| 4,943,280 | 7/1990 | Lander . |

(List continued on next page.)

FOREIGN PATENT DOCUMENTS

| | | |
|---|---|---|
| 2544262 | 4/1977 | Germany . |
| 878265 | 11/1981 | U.S.S.R. . |
| 897224 | 1/1982 | U.S.S.R. . |
| 1435246 | 11/1988 | U.S.S.R. . |
| 904635 | 8/1962 | United Kingdom . |
| 9304632 | 3/1993 | WIPO . |
| 9304715 | 3/1993 | WIPO . |
| 9304716 | 3/1993 | WIPO . |
| 9317626 | 9/1993 | WIPO . |

*Primary Examiner*—Guy V. Tucker

[57] ABSTRACT

A safety penetrating instrument for penetrating an anatomical cavity wall to gain access to an anatomical cavity includes a penetrating member having a distal end for penetrating the anatomical cavity wall, a distally-biased safety member having a distal end movable between an extended position where the safety member distal end protrudes distally from the penetrating member distal end to protect the distal end of the penetrating member and a retracted position where the safety member distal end is disposed proximally of the penetrating member distal end to expose the penetrating member distal end, an extending mechanism for moving the safety member to the extended position and for permitting the safety member to move proximally toward the retracted position, a handle or the like for manually moving the safety member proximally to the retracted position and a lock for locking the safety member in the retracted position to prevent movement of the safety member to the extended position during penetration of the anatomical cavity wall. The safety member can be a cannula, safety shield or probe, or both a cannula and a safety shield or probe. The safety penetrating instrument is responsive to movement of the penetrating member, cannula and/or the safety shield or probe distally toward retracted or rest positions to trigger release of the lock to permit the extending mechanism to move the safety member to the extended position.

66 Claims, 11 Drawing Sheets

U.S. PATENT DOCUMENTS

| | | |
|---|---|---|
| 5,030,206 | 7/1991 | Lander . |
| 5,053,016 | 10/1991 | Lander . |
| 5,066,288 | 11/1991 | Deniega et al. . |
| 5,073,169 | 12/1991 | Raiken . |
| 5,104,382 | 4/1992 | Brinkerhoff et al. . |
| 5,104,383 | 4/1992 | Shichman . |
| 5,114,407 | 5/1992 | Burbank . |
| 5,116,353 | 5/1992 | Green . |
| 5,122,122 | 6/1992 | Allgood . |
| 5,127,909 | 7/1992 | Schichman . |
| 5,152,754 | 10/1992 | Plyley et al. . |
| 5,158,552 | 10/1992 | Borgia et al. . |
| 5,207,647 | 5/1993 | Phelps . |
| 5,215,526 | 6/1993 | Deniega et al. . |
| 5,224,951 | 7/1993 | Freitas . |
| 5,224,952 | 7/1993 | Deniega et al. . |
| 5,226,426 | 7/1993 | Yoon . |
| 5,226,891 | 7/1993 | Bushatz et al. . |
| 5,246,425 | 9/1993 | Hunsberger et al. . |
| 5,248,298 | 9/1993 | Bedi et al. . |
| 5,256,148 | 10/1993 | Smith et al. . |
| 5,256,149 | 10/1993 | Banik et al. . |
| 5,261,891 | 11/1993 | Brinkerhoff et al. . |
| 5,267,965 | 11/1993 | Deniega . |
| 5,275,583 | 1/1994 | Crainich . |
| 5,290,243 | 3/1994 | Chodorow et al. . |
| 5,290,304 | 3/1994 | Storace . |
| 5,295,993 | 3/1994 | Green . |
| 5,312,354 | 3/1994 | Allen et al. . |
| 5,318,580 | 6/1994 | Gresl . |
| 5,318,585 | 6/1994 | Guy et al. . |
| 5,320,610 | 6/1994 | Yoon . |
| 5,324,268 | 6/1994 | Yoon . |
| 5,330,432 | 7/1994 | Yoon . |
| 5,336,176 | 8/1994 | Yoon . |
| 5,338,305 | 8/1994 | Plyley et al. . |
| 5,346,459 | 9/1994 | Allen . |
| 5,350,393 | 9/1994 | Yoon . |
| 5,360,405 | 11/1994 | Yoon . |
| 5,364,372 | 11/1994 | Danks et al. . |
| 5,366,445 | 11/1994 | Haber et al. . |
| 5,368,607 | 11/1994 | Freitas . |
| 5,372,588 | 12/1994 | Farley et al. . |
| 5,374,252 | 12/1994 | Banks et al. . |
| 5,376,082 | 12/1994 | Phelps . |
| 5,380,288 | 1/1995 | Hart et al. . |
| 5,383,859 | 1/1995 | Sewell, Jr. . |
| 5,431,635 | 7/1995 | Yoon ......................... 604/165 |

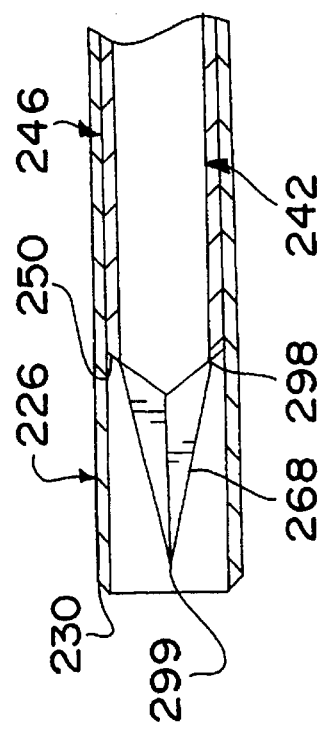
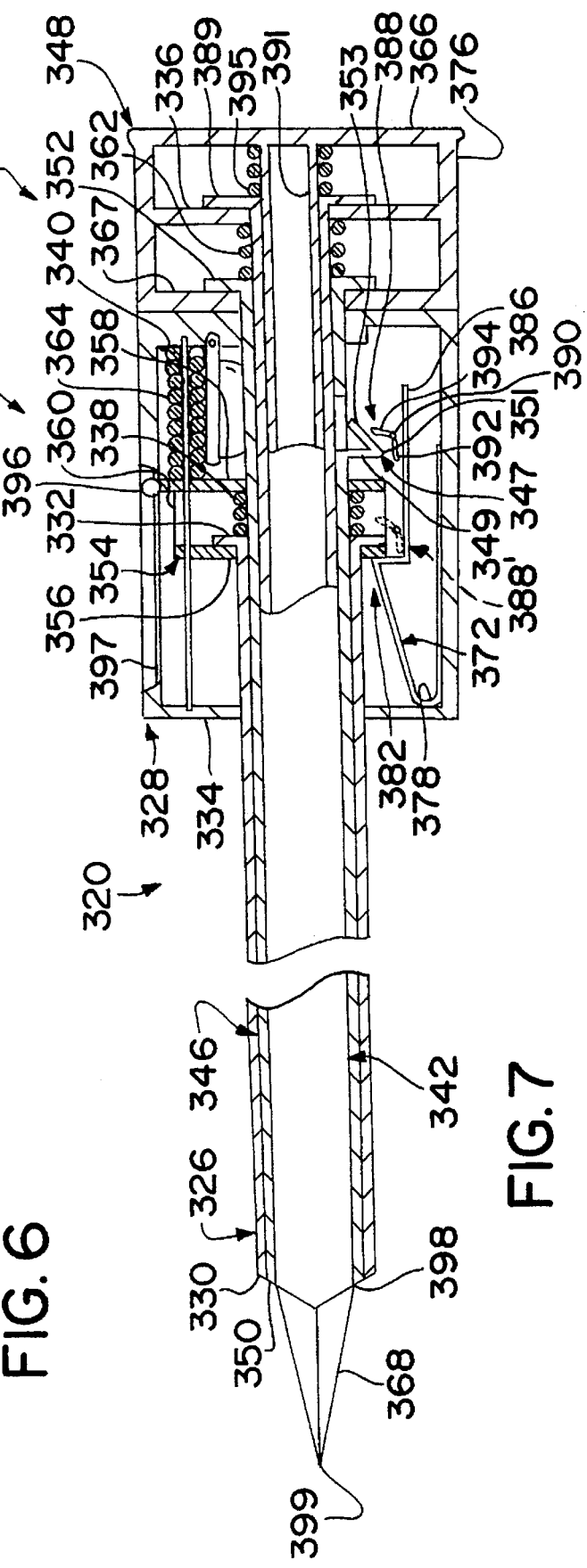
FIG. 6
FIG. 7

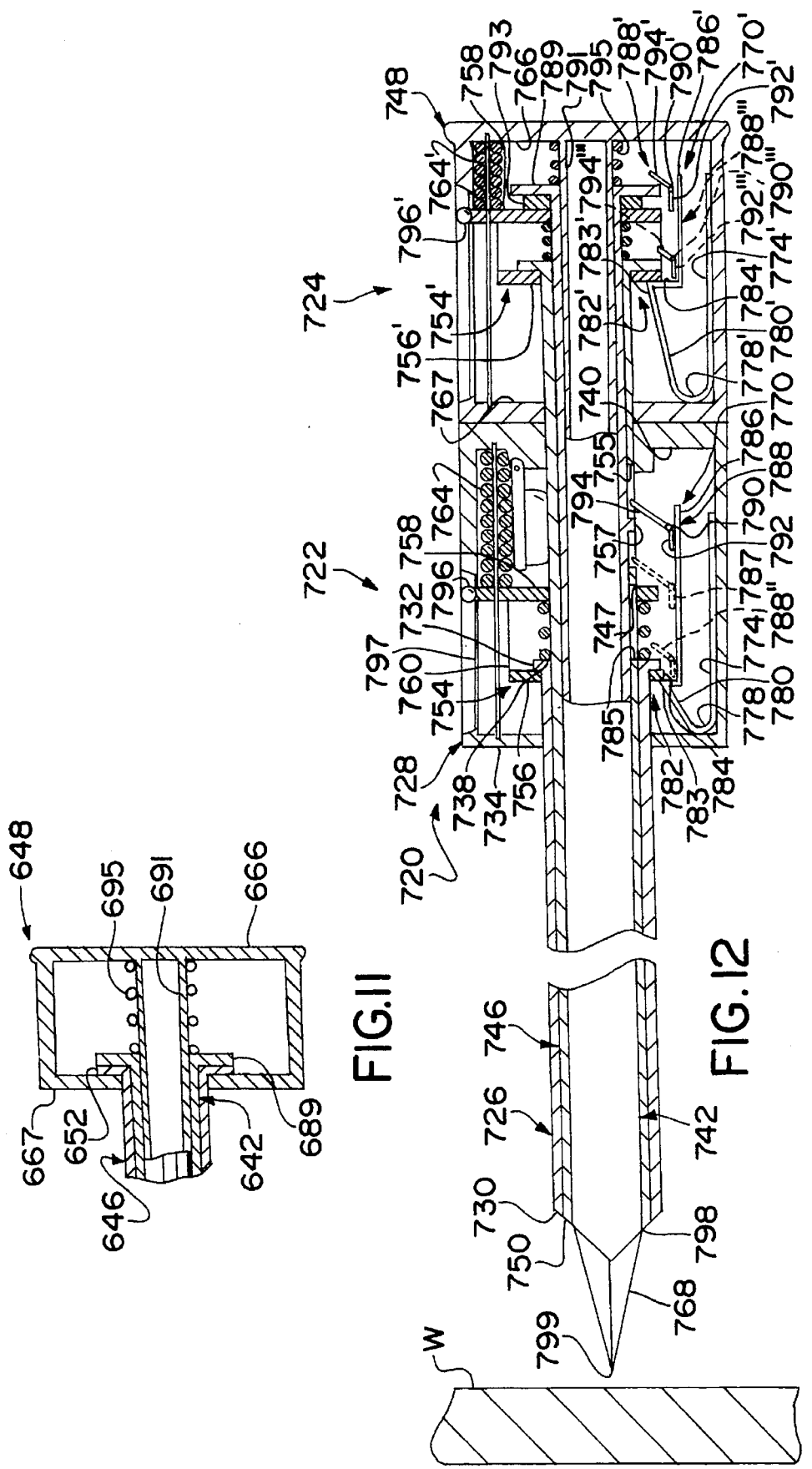

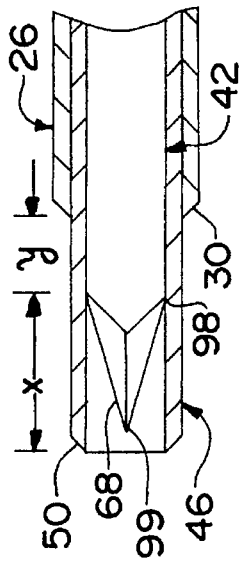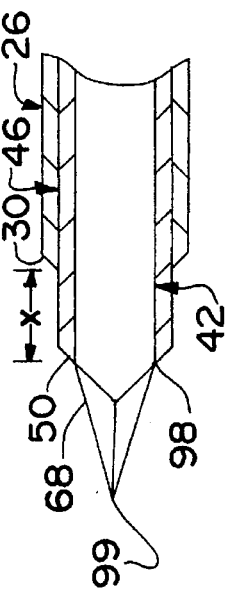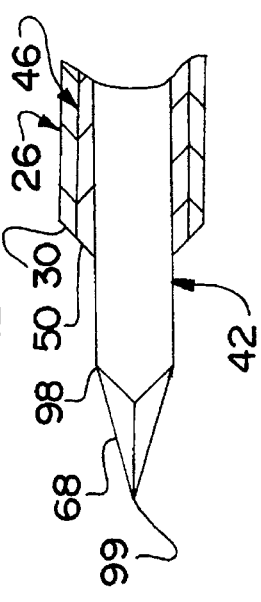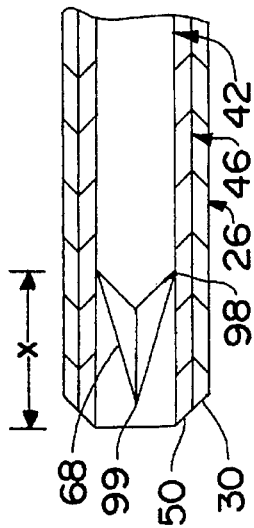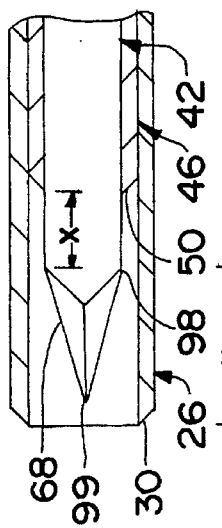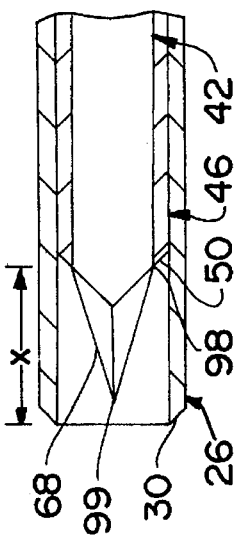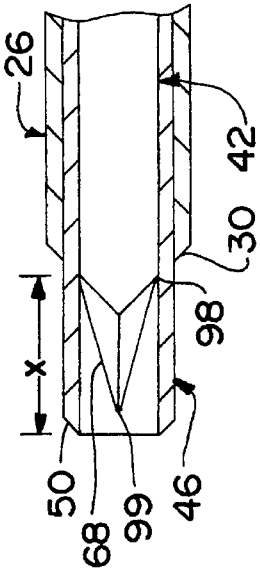

SAFETY PENETRATING INSTRUMENT WITH PENETRATING MEMBER, SAFETY MEMBER AND CANNULA MOVING DURING PENETRATION AND TRIGGERED SAFETY MEMBER PROTRUSION

CROSS-REFERENCE TO RELATED APPLICATIONS

This application is a continuation-in-part of prior applications Ser. No. 08/083,220, filed Jun. 24, 1993, now U.S. Pat. No. 5,431,635, Ser. No. 08/083,728, filed Jun. 29, 1993, now U.S. Pat. No. 5,466,224, and Ser. No. 08/115,152, filed Sep. 2, 1993, still pending, the disclosures of which are incorporated herein by reference.

BACKGROUND OF THE INVENTION

1. Field of the Invention

The present invention pertains to safety penetrating instruments and, more particularly, to safety penetrating instruments for use in forming portals for establishing communication with anatomical cavities wherein tissue and organ structures are protected from the tips of the penetrating members and to methods of penetrating anatomical cavity walls with safety penetrating instruments.

2. Discussion of the Prior Art

Penetrating instruments are widely used in medical procedures to gain access to anatomical cavities ranging in size from the abdomen to small blood vessels, such as veins and arteries, epidural, pleural and subarachnoid spaces, heart ventricles and spinal and synovial cavities. Use of penetrating instruments has become an extremely popular and important first step in endoscopic, or minimally invasive, surgery to establish an endoscopic portal for many various procedures, such as laparoscopic procedures in the abdominal cavity. Such penetrating instruments typically include a cannula or portal sleeve and a penetrating member disposed within the cannula and having a sharp tip for penetrating an anatomical cavity wall with the force required to penetrate the cavity wall being dependent upon the type and thickness of the tissue forming the cavity wall. Once the wall is penetrated, it is desirable to protect the sharp tip of the penetrating member from inadvertent contact with or injury to tissue or organ structures in or forming the cavity in that, once penetration is achieved, the lack of tissue resistance can result in the sharp tip traveling too far into the cavity and injuring adjacent tissue or organ structures.

Various safety penetrating instruments have been proposed, generally falling into protruding and retracting categories. In protruding safety penetrating instruments, a safety member is spring biased to protrude beyond the tip of the penetrating member in response to the reduced force on the distal end of the safety member upon entry into the anatomical cavity. The safety member can be disposed around the penetrating member in which case the safety member is frequently referred to as a shield, or the safety member can be disposed within the penetrating member in which case the safety member is frequently referred to as a probe. In retracting safety penetrating instruments, the penetrating member is retracted into the cannula upon entry into the anatomical cavity in response to distal movement of a component of the safety penetrating instrument such as the penetrating member, the cannula, a probe or a safety member such as a shield or probe.

While protruding safety penetrating instruments have been well received, there is room for improvement in reducing the force required to penetrate the cavity wall which necessarily includes the force required to overcome the spring bias on the safety member as well as the resistance of the cavity wall and insuring that the safety member protrudes which normally requires increasing the spring bias on the safety member and, thus, the force to penetrate. Retracting safety penetrating instruments have the disadvantages of requiring relatively complex mechanisms to hold the penetrating member in an extended position during penetration and to release the penetrating member for retraction and, concomitantly, not retracting sufficiently quickly and reliably.

SUMMARY OF THE INVENTION

Accordingly, it is a primary object of the present invention to improve safety penetrating instruments of the type having a penetrating member and a safety member biased distally to protrude beyond the distal end of the penetrating member by easing penetration and assuring protrusion of the safety member.

Another object of the present invention is to reduce the force-to-penetrate required to penetrate an anatomical cavity wall with a safety penetrating instrument of the type having a distally biased safety member for protruding beyond a distal end of a penetrating member once penetration into the cavity has been achieved.

A further object of the present invention is to increase the force biasing a safety member distally in a safety penetrating instrument to assure protrusion of the safety member after penetration into an anatomical cavity without increasing the force-to-penetrate required for penetration.

The present invention has an additional object to permit proximal movement of the penetrating member, cannula and safety shield or probe of a safety penetrating instrument during penetration of an anatomical cavity wall and to utilize the safety shield or probe as a safety member triggered to move distally from a retracted position exposing the distal end of the penetrating member to an extended protruding position protecting the penetrating member distal end in response to distally-biased movement of the safety shield or probe upon entering the anatomical cavity.

Another object of the present invention is to permit proximal movement of the penetrating member, cannula and safety shield or probe of a safety penetrating instrument during penetration of an anatomical cavity wall and to utilize the safety shield or probe as a safety member triggered to move distally from a retracted position exposing the distal end of the penetrating member to an extended protruding position protecting the penetrating member distal end in response to distally-biased movement of the cannula upon entering the anatomical cavity.

It is another object of the present invention to permit proximal movement of the penetrating member, cannula and safety shield or probe of a safety penetrating instrument during penetration of an anatomical cavity wall and to utilize the safety shield or probe as a safety member triggered to move distally from a retracted position exposing the distal end of the penetrating member to an extended protruding position protecting the penetrating member distal end in response to distally-biased movement of the penetrating member upon entering the anatomical cavity.

Yet another object of the present invention is to permit proximal movement of the penetrating member, cannula and safety shield or probe of a safety penetrating instrument during penetration of an anatomical cavity wall and to utilize the safety shield or probe as a safety member triggered to move distally from a retracted position exposing the distal end of the penetrating member to an extended protruding position protecting the penetrating member distal end in response to distally-biased movement of both the cannula and safety shield or probe upon entering the anatomical cavity.

A further object of the present invention is to permit proximal movement of the penetrating member, cannula and safety shield or probe of a safety penetrating instrument during penetration of an anatomical cavity wall and to utilize the safety shield or probe as a safety member triggered to move distally from a retracted position exposing the distal end of the penetrating member to an extended protruding position protecting the penetrating member distal end in response to distally-biased movement of the safety member and penetrating member upon entering the anatomical cavity.

Yet another object of the present invention is to permit proximal movement of the penetrating member, cannula and safety shield or probe of a safety penetrating instrument during penetration of an anatomical cavity wall and to utilize the safety shield or probe as a safety member triggered to move distally from a retracted position exposing the distal end of the penetrating member to an extended protruding position protecting the penetrating member distal end in response to distally-biased movement of the cannula and penetrating member upon entering the anatomical cavity.

A still further object of the present invention is to permit proximal movement of the penetrating member, cannula and safety shield or probe of a safety penetrating instrument during penetration of an anatomical cavity wall and to utilize the safety shield or probe as a safety member triggered to move distally from a retracted position exposing the distal end of the penetrating member to an extended protruding position protecting the penetrating member distal end in response to distally-biased movement of the safety shield or probe, penetrating member and cannula upon entering the anatomical cavity.

An additional object of the present invention is to permit proximal movement of the penetrating member, cannula and safety shield or probe of a safety penetrating instrument during penetration of an anatomical cavity wall and to utilize the cannula as a safety member triggered to move distally from a retracted position exposing the distal end of the penetrating member to an extended protruding position protecting the penetrating member distal end in response to distally-biased movement of the cannula upon entering the anatomical cavity.

Still another object of the present invention is to permit proximal movement of the penetrating member, cannula and safety shield or probe of a safety penetrating instrument during penetration of an anatomical cavity wall and to utilize the cannula as a safety member triggered to move distally from a retracted position exposing the distal end of the penetrating member to an extended protruding position protecting the penetrating member distal end in response to distally-biased movement of the safety shield or probe upon entering the anatomical cavity.

Another object of the present invention is to permit proximal movement of the penetrating member, cannula and safety shield or probe of a safety penetrating instrument during penetration of an anatomical cavity wall and to utilize the cannula as a safety member triggered to move distally from a retracted position exposing the distal end of the penetrating member to an extended protruding position protecting the penetrating member distal end in response to distally-biased movement of the penetrating member upon entering the anatomical cavity.

Yet a further object of the present invention is to permit proximal movement of the penetrating member, cannula and safety shield or probe of a safety penetrating instrument during penetration of an anatomical cavity wall and to utilize the cannula as a safety member triggered to move distally from a retracted position exposing the distal end of the penetrating member to an extended protruding position protecting the penetrating member distal end in response to distally-biased movement of both the cannula and safety shield or probe upon entering the anatomical cavity.

Still another object of the present invention is to permit proximal movement of the penetrating member, cannula and safety shield or probe of a safety penetrating instrument during penetration of an anatomical cavity wall and to utilize the cannula as a safety member triggered to move distally from a retracted position exposing the distal end of the penetrating member to an extended protruding position protecting the penetrating member distal end in response to distally-biased movement of the cannula and penetrating member upon entering the anatomical cavity.

An additional object of the present invention is to permit proximal movement of the penetrating member, cannula and safety shield or probe of a safety penetrating instrument during penetration of an anatomical cavity wall and to utilize the cannula as a safety member triggered to move distally from a retracted position exposing the distal end of the penetrating member to an extended protruding position protecting the penetrating member distal end in response to distally-biased movement of the penetrating member or safety shield or probe upon entering the anatomical cavity.

Another object of the present invention is to permit proximal movement of the penetrating member, cannula and safety shield or probe of a safety penetrating instrument during penetration of an anatomical cavity wall and to utilize the cannula as a safety member triggered to move distally from a retracted position exposing the distal end of the penetrating member to an extended protruding position protecting the penetrating member distal end in response to distally-biased movement of the penetrating member, safety shield or probe and cannula upon entering the anatomical cavity.

A further object of the present invention is to permit proximal movement of the penetrating member, cannula and safety shield or probe of a safety penetrating instrument during penetration of an anatomical cavity wall and to utilize both the cannula and safety shield or probe as safety members triggered to move distally from retracted positions exposing the distal end of the penetrating member to extended protruding positions protecting the penetrating member distal end in response to distally-biased movement of the safety shield or probe upon entering the anatomical cavity.

It is also an object of the present invention to permit proximal movement of the penetrating member, cannula and safety shield or probe of a safety penetrating instrument during penetration of an anatomical cavity wall and to utilize both the cannula and safety shield or probe as safety members triggered to move distally from retracted positions exposing the distal end of the penetrating member to extended protruding positions protecting the penetrating member distal end in response to distally-biased movement of the cannula upon entering the anatomical cavity.

Still another object of the present invention is to permit proximal movement of the penetrating member, cannula and safety shield or probe of a safety penetrating instrument during penetration of an anatomical cavity wall and to utilize both the cannula and safety shield or probe as safety members triggered to move distally from retracted positions exposing the distal end of the penetrating member to extended protruding positions protecting the penetrating member distal end in response to distally-biased movement of the penetrating member upon entering the anatomical cavity.

An additional object of the present invention is to permit proximal movement of the cannula and safety shield or probe of a safety penetrating instrument during penetration of an anatomical cavity wall and to utilize both the cannula and safety shield or probe as safety members triggered to move distally from retracted positions exposing the distal end of the penetrating member to extended protruding positions covering the penetrating member distal end in response to distally-biased movement of both the cannula and safety shield or probe upon entering the anatomical cavity.

Another object of the present invention is to permit proximal movement of the penetrating member, cannula and safety shield or probe of a safety penetrating instrument during penetration of an anatomical cavity wall and to utilize both the cannula and safety shield or probe as safety members triggered to move distally from retracted positions exposing the distal end of the penetrating member to extended protruding positions protecting the penetrating member distal end in response to distally-biased movement of the penetrating member and safety shield or probe upon entering the anatomical cavity.

A further object of the present invention is to permit proximal movement of the penetrating member, cannula and safety shield or probe of a safety penetrating instrument during penetration of an anatomical cavity wall and to utilize both the cannula and safety shield or probe as safety members triggered to move distally from retracted positions exposing the distal end of the penetrating member to extended protruding positions protecting the penetrating member distal end in response to distally-biased movement of the cannula and penetrating member upon entering the anatomical cavity.

Still another object of the present invention is to permit proximal movement of the penetrating member, cannula and safety shield or probe of a safety penetrating instrument during penetration of an anatomical cavity wall and to utilize both the cannula and safety shield or probe as safety members triggered to move distally from retracted positions exposing the distal end of the penetrating member to extended protruding positions protecting the penetrating member distal end in response to distally-biased movement of the penetrating member, cannula and safety shield or probe upon entering the anatomical cavity.

Some of the advantages of the safety penetrating instrument of the present invention are that the distal extending force on a safety member can be designed to assure protrusion of the safety member upon penetration regardless of the anatomical cavity being penetrated, that the force-to-penetrate of a safety penetrating instrument can be minimized to permit use in delicate tissue, that release of the safety member for movement to the extended protruding position can be triggered by distally biased movement of a penetrating member, cannula and/or a safety shield or probe in response to penetration through the tissue, and that the safety penetrating instrument can be inexpensively manufactured with minimum components to reduce cost, facilitate sterilization for re-use and allow economical single-patient use.

The present invention is generally characterized in a safety penetrating instrument including a penetrating member having a distal end for penetrating an anatomical cavity wall to gain access to an anatomical cavity, a safety member having a distal end movable between an extended position where the safety member distal end is disposed distally of the penetrating member distal end to protect the penetrating member distal end and a retracted position where the safety member distal end is disposed proximally of the penetrating member distal end to expose the penetrating member distal end, extending means for moving the safety member distally to the extended position and for permitting the safety member to move proximally to the retracted position, means for manually moving the safety member proximally from the extended position to the retracted position and locking means for locking the safety member in the retracted position to prevent movement of the safety member to the extended position during penetration of the anatomical cavity wall. The safety member can be a cannula and/or a safety shield or probe biased distally in the retracted position to be movable proximally from the retracted position during penetration of the anatomical cavity wall by the safety penetrating instrument and distally toward the retracted position upon penetration into the anatomical cavity by the safety penetrating instrument. Releasing means responsive to distally biased movement of the penetrating member, cannula and/or the safety shield or probe upon penetration into the anatomical cavity triggers release of the locking means to permit the extending means to move the safety member to the extended position.

Other objects and advantages of the present invention will become apparent from the following description of the preferred embodiments taken in conjunction with the accompanying drawings wherein, unless specified otherwise, like parts or parts that perform like functions are identified in each of the several figures by the same reference character or by reference characters sharing the same last two digits.

BRIEF DESCRIPTION OF THE DRAWINGS

FIG. 6 is a side view, partly in section, of the distal end of the safety penetrating instrument of FIG. 5 following penetration into the anatomical cavity.

FIG. 7 is a broken side view, partly in section, of a further modification of a safety penetrating instrument according to the present invention.

FIG. 11 is a fragmentary side view, partly in section, illustrating a modified hub for a safety penetrating instrument according to the present invention.

FIG. 12 is a broken side view, partly in section, illustrating a further modification of the safety penetrating instrument of the present invention.

FIGS. 13–20 are fragmentary side views, partly in section, of alternative distal configurations for the safety penetrating instruments of the present invention.

DESCRIPTION OF THE PREFERRED EMBODIMENTS

The safety penetrating instrument of the present invention is described hereinafter for use as an instrument for inserting a portal sleeve through a wall of an anatomical cavity to form a portal for the introduction of various surgical and diagnostic instruments into the cavity during endoscopic procedures, such as laparoscopy. It is understood, however, that the safety penetrating instrument of the present invention can be used for safe penetration or introduction into anatomical cavities of needles with fluid flow therethrough and catheters as well as for other instruments engaging tissue during surgical or diagnostic procedures. Accordingly, the cannula or outer tubular member of the safety penetrating instrument can be a portal sleeve, a needle, a catheter or a tubular component of a medical instrument.

Figure 1:
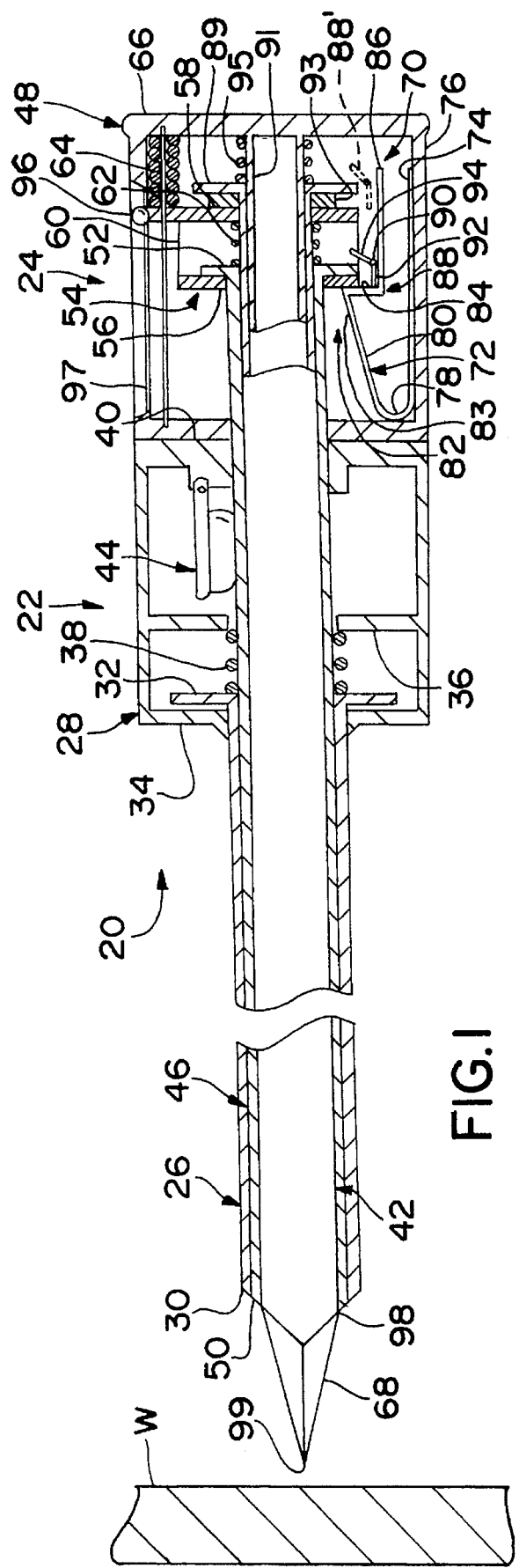
FIG. 1 is a broken side view, partly in section, of a safety penetrating instrument according to the present invention.

A safety penetrating instrument 20 according to the present invention, as shown in FIG. 1, includes a portal unit 22 and a penetrating unit 24. The portal unit 22 can be made of any desirable, medical grade materials depending on procedural use and desirability of being for single patient use or re-usable. The portal unit 22 includes an elongate portal sleeve, cannula or catheter 26 and a housing 28 mounting a proximal end of portal sleeve 26. Portal sleeve 26 terminates distally at a distal end 30 and proximally at a flange 32 disposed between front wall 34 of housing 28 and a transverse wall or partition 36 proximally spaced from front wall 34. A bias member 38 is connected between portal sleeve flange 32 and the transverse wall 36 to bias the portal sleeve distally. As shown, bias member 38 includes a helical coil spring disposed around the longitudinal axis of the safety penetrating instrument and mounted in compression between flange 32 and transverse wall 36 to bias the portal sleeve 26 distally to cause flange 32 to abut the front wall 34 of housing 28. However, bias member 38 can include various other types of springs as well as other types of bias devices including compression springs, tension springs, torsion springs, pan springs, leaf springs, rubber, plastic or magnets, for example. Portal sleeve 26 can have any desirable cross-sectional configuration, including cylindrical or tubular configurations, in accordance with the procedure to be performed and the anatomical cavity to be penetrated. Preferably, portal sleeve 26 is made of a substantially cylindrical length of rigid or flexible and transparent or opaque material, such as stainless steel or other medically acceptable plastic or metal material, and has a tubular configuration defining a lumen between the distal and proximal portal sleeve ends for receiving a penetrating member 42 of penetrating unit 24.

Housing 28 can be made of any desirable material and can have any desirable configuration to facilitate grasping by a surgeon and includes a rear wall 40 having an opening therein aligned with an opening in the housing front wall 34 to allow passage therethrough by the penetrating member 42. The housing 28 is preferably constructed to sealingly engage instruments passing therethrough and to include a valve 44 biased to a closed state when no instrument passes through the portal sleeve. A flapper valve 44 is shown; however, any suitable valve construction can be utilized, including trumpet or nipple valves.

Penetrating unit 24 includes penetrating member 42, safety shield 46 and hub 48 mounting proximal ends of the penetrating member and the safety shield. Housing rear wall 40 is configured for receiving hub 48; and when the hub is mated with the housing as shown, safety shield 46 is disposed between penetrating member 42 and portal sleeve 26. The safety shield 46 terminates distally at a distal end 50 and proximally at a transverse flange 52 disposed between walls of a rail member 54 mounted in hub 48. Rail member 54 is movable within hub 48 and is generally U-shaped including a forward wall 56 disposed transverse or perpendicular to a longitudinal axis of the penetrating instrument, a rearward wall 58 in configuration parallel to forward wall 56 and a side wall 60 transversely joining the forward and rearward rail member walls. Flange 52 is disposed between the rail member forward and rearward walls with the rail member forward wall 56 having an opening therein allowing passage therethrough by the safety shield 46. The rail member forward and rearward walls are disposed parallel or substantially parallel to flange 52, and a bias member 62 is connected between safety shield flange 52 and the rail member rearward wall 58 to bias the safety shield distally. As shown, bias member 62 includes a helical coil spring disposed around the penetrating member 42 and mounted in compression between flange 52 and the rail member rearward wall 58 to bias the safety shield 46 distally to cause flange 52 to abut the rail member forward wall 56. However, bias member 62 can include various other types of springs as well as other types of bias devices including compression springs, tension springs, torsion springs, pan springs, leaf springs, rubber, plastic or magnets, for example. An extending member 64 is mounted between rail member rearward wall 58 and a rear wall 66 of hub 48 to bias the safety shield 46 in a distal direction to an extended protruding position where distal end 50 of the safety shield is disposed beyond a distal end 68 of the penetrating member 42 as will be explained further below. The extending member 64 includes a helical coil spring mounted in compression between the rail member rearward wall 58 and the rear wall 66 of the hub to bias the rail member 54 and, therefore, the safety shield 46, in a distal direction to an extended protruding position where the distal end 50 of the safety shield is disposed beyond the distal end 68 of the penetrating member.

A locking and releasing mechanism 70 for locking the safety shield in a retracted position, shown in FIG. 1, exposing the distal end 68 of the penetrating member and for releasing the rail member 54 to allow the safety shield 46 to move to the extended protruding position includes a latch or locking spring 72, made of a strip of resilient material, formed to have a substantially flat base 74 secured to a bottom wall 76 of hub 48 and a bend 78 joining the base 74 with an upwardly angled arm 80 spaced from the base. Arm 80 carries or forms a latch 82 having a distal angled latching surface 83 joining a proximal latching surface 84 disposed substantially transverse to the longitudinal axis of the safety penetrating instrument and substantially parallel to the rail member forward wall 56. Arm 80 has an extension 86 positioned proximally of latch 82, and a releasing member or trigger 88 is juxtaposed with extension 86. The trigger 88 is pivotally mounted in the hub on a pin 90 secured to a wall or walls of the hub or structure supported in the hub, and the trigger is generally L-shaped with a leg 92 overlying extension 86 and a leg 94 extending transversely from leg 92 but at a slight angle toward the proximal end of the safety penetrating instrument. A torsion spring (not shown) is coiled around pin 90 and fixed to trigger 88 to bias the trigger counterclockwise, looking at FIG. 1, such that leg 92 is biased toward extension 86.

A handle 96 is coupled with the safety shield 46, such as with flange 52 or the rearward wall of rail member 54 as shown, for movement along a slot 97 formed in a top wall of the hub 48 to move the safety shield from the extended protruding position to the locked retracted position as previously explained above.

Penetrating member distal end 68 extends distally from a transverse dimensional transition 98 terminating in a sharp tip 99 and the proximal end of the penetrating member carries or forms a flange 89. A guide tube 91 extends from hub rear wall 66 in a distal direction and is telescopically received within the penetrating member to allow sliding movement of the penetrating member over the tube. A stop 93 formed by an internal wall or partition in the hub has an opening therein for passage of the penetrating member while serving to limit distal movement of the penetrating member by obstructing flange 89. A bias member 95 is disposed around the guide tube 91 and held in compression between the penetrating member flange and the hub rear wall to bias the penetrating member distally toward a rest position where flange 89 abuts stop 93.

The portal unit 22 and the penetrating unit 24 can be provided separately or assembled together as shown in FIG. 1, and either or both of the portal and penetrating units can be manufactured in a manner to be disposable for single patient use or to be sterilizable for re-use. The hub 48 can be coupled to the housing 28 by suitable detent or latch mechanisms if desired, and the penetrating unit can be withdrawn from the portal unit leaving the portal sleeve 26 in place within an anatomical cavity.

Figure 3:
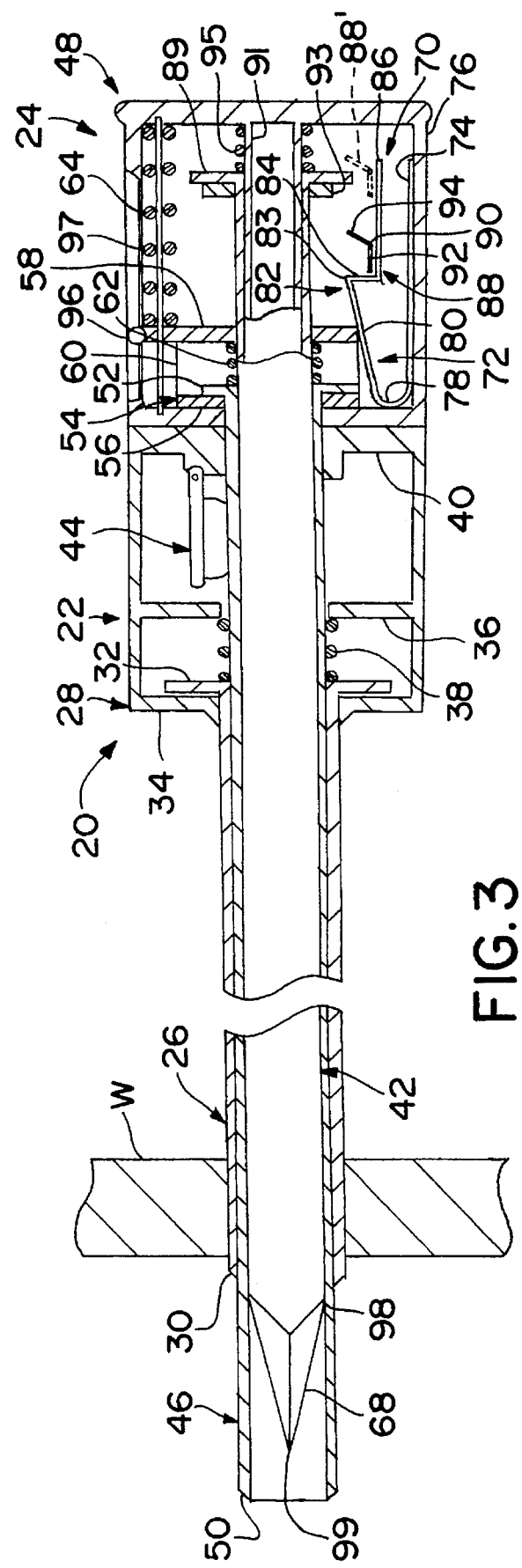
FIG. 3 is a broken side view, partly in section, of the safety penetrating instrument of FIG. 1 following penetration into the anatomical cavity.

In use, the safety shield 46 of safety penetrating instrument 20 will initially be in the extended protruding position shown in FIG. 3 with the safety shield distal end 50 disposed beyond the distal end 68 of penetrating member 42 to protect the sharp tip of the penetrating member. In order to move the safety shield to the retracted position shown in FIG. 1, the handle 96 is grasped to move the safety shield proximally until the rail member forward wall 56 rides over latch 82 to be latched in the retracted position with the rail member forward wall 56 locked against proximal latching surface 84. The user can feel the rail member forward wall 56 lock into place in engagement with the latch 82 and can also visually determine that the safety shield is in the locked retracted position by noting the position of the handle 96 at a proximal end of the slot.

Figure 2:
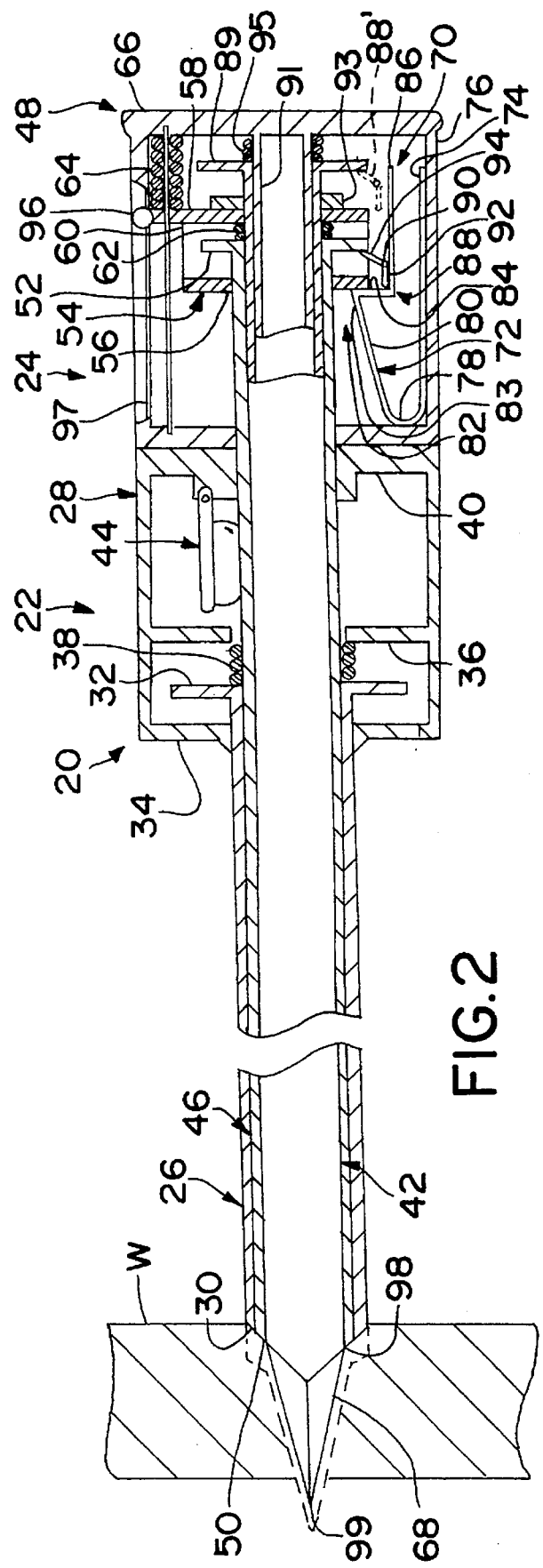
FIG. 2 is a broken side view, partly in section, of the safety penetrating instrument of FIG. 1 during penetration of a wall of an anatomical cavity.

With the safety shield 46 in the locked retracted position illustrated in FIG. 1, the portal sleeve and safety shield distal ends 30 and 50 will be disposed proximally of the distal tip 99 of the penetrating member in alignment with the transverse dimensional transition 98. Penetration of the cavity wall W is commenced, and the force from tissue contact on the penetrating member, portal sleeve and safety shield distal ends 68, 30 and 50 will cause the penetrating member, portal sleeve and safety shield to move together proximally against the bias of respective bias members 95, 38 and 62 thereby easing penetration. Safety shield flange 52 will also move past trigger leg 94. Movement of flange 52 proximally past trigger leg 94 does not cause movement of latch 82 since there is no contact of trigger leg 92 with arm extension 86; and, accordingly, flange 52 is now positioned proximally of trigger leg 94 as shown in FIG. 2.

Upon entry into the anatomical cavity, the counter force on the penetrating member, portal sleeve and safety shield distal ends caused by tissue contact will be reduced allowing bias members 95, 38 and 62 to move the penetrating member, portal sleeve and safety shield distally. Distal movement of the safety shield causes flange 52 to engage trigger leg 94 and to pivot the trigger counterclockwise looking at FIG. 2 causing leg 92 to engage arm extension 86. The engagement of leg 92 with arm extension 86 causes arm 80 to move toward base 74 moving the latch 82 out of engagement with the rail member forward wall 56 thereby allowing spring 64 to cause the safety shield to move further distally to the extended protruding position wherein safety shield distal end 50 protrudes beyond the distal end 68 of the penetrating member as shown in FIG. 3. The penetrating unit 24 including the penetrating member 42 and the safety shield 46 can then be withdrawn from the portal unit 22 leaving the portal sleeve 26 in place to serve as a portal for introducing medical instruments therethrough.

Alternatively or in addition to trigger 88, a second trigger 88' can be provided as shown in phantom in FIG. 1 for being engaged by the penetrating member flange 89. If trigger 88' is mounted in the hub without trigger 88, movement of the safety shield to the extended protruding position will be triggered by distally-biased movement of the penetrating member upon penetrating into an anatomical cavity. If both triggers are mounted in the hub, it will be appreciated that counterclockwise rotation of either trigger will result in latch 82 being moved away from rail member 54 to release the rail member and safety shield thereby allowing the extending member 64 to move the safety shield distally to the extended protruding position in response to distally-biased movement of either the safety shield or the penetrating member.

Figure 4:
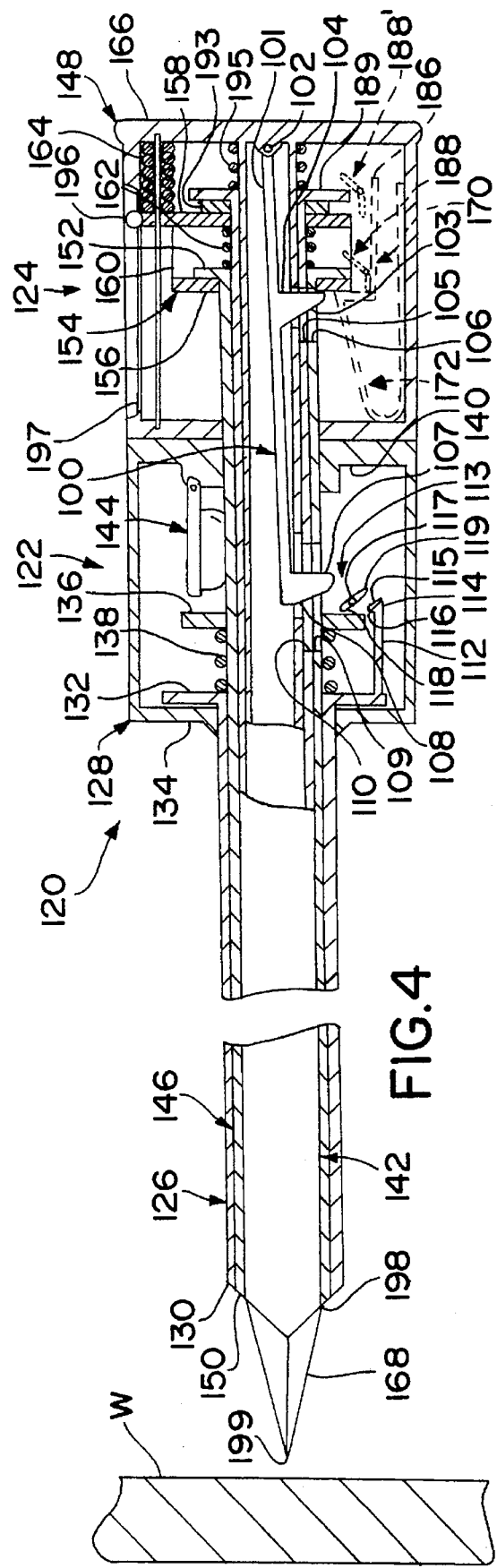
FIG. 4 is a broken side view, partly in section, of a modification of a safety penetrating instrument according to the present invention.

A modification of the safety penetrating instrument of the present invention is shown in FIG. 4 at 120. The modified safety penetrating instrument 120 is similar to safety penetrating instrument 20 except that movement of the safety shield to the extended protruding position is triggered by distally-biased movement of the portal sleeve in response to a reduction in the force from tissue contact following entry into the anatomical cavity. Safety penetrating instrument 120 includes a portal unit 122 and a penetrating unit 124, the penetrating unit 124 being similar to penetrating unit 24 and including a penetrating member 142, a safety shield 146 and a hub 148 mounting proximal ends of the penetrating member and safety shield. Safety shield 146 is similar to safety shield 46 and terminates distally at a distal end 150 and proximally at a transverse flange or plate 152 disposed between forward and rear walls 156 and 158 of a rail member 154. Penetrating member 142 is hollow and includes a flange 189 at a proximal end disposed between a stop 193 and rear wall 166 of hub 148. The bias member 162 is similar to bias member 62 and is disposed around penetrating member 142 and held in compression between the safety shield flange 152 and the rear wall of rail member 154. An extending member 164, similar to extending member 64, is held in compression between rail member rear wall 158 and hub rear wall 166.

Rail member 154 is locked in the retracted position shown in FIG. 4 by a longitudinal latch arm 100 disposed within the penetrating member 142 and having a proximal end 101 pivotally mounted on a pin 102 secured to the rear wall 166 of the hub. A torsion spring or the like (not shown) is connected between the pin 102 and latch arm 100 or between the penetrating member inner wall and latch arm 100 to bias the arm 100 in a counterclockwise direction looking at FIG. 4. Latch arm 100 carries a latching protrusion 103 with a transverse latching surface 104 configured to extend through aligned slots 105 and 106 formed in the penetrating member and safety shield, respectively, to engage rail member forward wall 156. Slot 106 formed in safety shield 146 is oriented along a longitudinal axis of the safety shield and is sufficiently long to allow movement of the safety shield flange 152 between forward and rear rail member walls 156 and 158. Slot 105 formed in penetrating member 142 is oriented along a longitudinal axis of the penetrating member and is sufficiently long to allow movement of the penetrating member flange 189 between transverse stop 193 and hub rear wall 166. A triggering protrusion 107 is formed at a distal end of the latch arm 100 and includes a curved distal edge 108 that protrudes through aligned slots 109 and 110 formed in penetrating member 142 and safety shield 146 distally of slots 105 and 106 to communicate into housing 128. Penetrating member slot 109 and safety shield slot 110 are sufficiently long to allow movement of the penetrating member flange and safety shield flange within the hub.

Portal unit 122 is similar to portal unit 22 for safety penetrating instrument 20 and, in addition, includes a finger 112 extending perpendicularly from the portal sleeve flange 132 in a proximal direction and a lever 113 disposed between finger 112 and triggering protrusion 107. Finger 112 terminates proximally in a barb 114 with an acutely angled leading edge 115 and a vertical or transverse trailing edge 116 parallel to flange 132. Lever 113 is pivotally mounted on a pin 117 secured to a wall or walls of housing 128 perpendicular to the longitudinal axis of the penetrating instrument, and includes axially opposed ends 118 and 119. Finger 112 is positioned on flange 132 in a manner to engage lower end 119 of lever 113 when moved proximally. Upper end 118 of lever 113 is rotatable in a clockwise direction to contact triggering protrusion 107.

Use of the safety penetrating instrument 120 is similar to that described above with respect to safety penetrating instrument 20 in that, when the user desires to penetrate into an anatomical cavity, the safety penetrating instrument will normally be provided with the safety shield 146 in the extended position where the distal end 150 of the safety shield protrudes beyond the penetrating member distal end 168. Penetrating member 142 will normally be in a rest position where the penetrating member flange 189 abuts stop 193 under the influence of bias member 195. Additionally, the portal sleeve 126 will be provided in a rest position where the distal end 130 of the portal sleeve is aligned with the penetrating member distal transition 198 and the portal sleeve flange 132 abuts the housing front wall 134. In the portal sleeve rest position, barb 114 of finger 112 will be disposed distally of lever lower end 119. The safety shield 146 is biased to the extended protruding position by extending member 164 with handle 196 being disposed at a distal end of the slot 197 in the hub 176.

Prior to commencing penetration of an anatomical cavity wall, handle 196 is grasped and manually moved proximally to move safety shield 146 proximally against the bias of extending member 164 until rail member forward wall 156 rides over latching protrusion 103 by engaging an angled distal surface of the latching protrusion 103 to cam the latch arm 100 in a clockwise direction looking at FIG. 4. When rail member forward wall 156 moves proximally past latching surface 104, latch arm 100 springs back in a counterclockwise direction to lock the rail member 154 and safety shield 146 mounted thereby in the retracted position shown in FIG. 4. The user can feel the rail member lock into place in engagement with latch arm 100 and can also visually determine that the safety shield is in the locked retracted position by noting the position of the handle 196 at a proximal end of the slot. With the safety shield 146 locked in the retracted position, the distal end 150 of the safety shield will be disposed adjacent the transverse dimensional transition 198 of the penetrating member 142, the distal end 130 of the portal sleeve 126 will be disposed adjacent the dimensional transition 198 as well, and portal sleeve flange 132 will remain biased by spring 138 into abutment with housing forward wall 134.

With the safety penetrating instrument 120 in the position illustrated in FIG. 4, penetration of the anatomical cavity wall is commenced, and the force from tissue contact on the penetrating member, portal sleeve and safety shield distal ends 168, 130 and 150 will cause the penetrating member, portal sleeve and safety shield to move together proximally against the bias of springs 195, 138 and 162, respectively. Proximal movement of the portal sleeve 126 also causes barb 114 carried by finger 112 to contact and move past lever lower end 119 causing lever 113 to rotate counterclockwise. Lever upper end 118 is thus moved away from triggering protrusion 107 without causing any movement of latch arm 100. Accordingly, the barb 114 will then move past the lower end 119 of the lever to be positioned proximally of the lever lower end. Upon entry into the anatomical cavity, the counter force on the distal end of the portal sleeve will be reduced allowing spring 138 to move the portal sleeve distally causing barb 114 to engage lever lower end 119 and thereby to pivot the lever 113 clockwise causing lever upper end 118 to engage triggering protrusion 107. The engagement of lever 113 with triggering protrusion 107 causes lever arm 100 to rotate clockwise moving the latching protrusion 103 out of engagement with rail member forward wall 156 thereby allowing extending member 164 to cause the safety shield to move distally to the extended protruding position shown in FIG. 3 wherein the safety shield distal end 150 protrudes beyond the distal end 168 of penetrating member 142. The penetrating unit 124 can then be withdrawn from the portal unit 122 leaving the portal sleeve 126 in place for the introduction of medical instruments therethrough.

Another modification of the safety penetrating instrument of the present invention is arrived at by combining the locking and releasing mechanisms of safety penetrating instruments 20 and 120 to permit movement of the safety shield to the extended protruding position in response to distally-biased movement of at least one of the portal sleeve, penetrating member and safety shield. The modification involves mounting a locking and releasing mechanism for engaging the rail member 154 in hub 148 of safety penetrating instrument 120 as shown in phantom at 170 in FIG. 4. The locking and releasing mechanism 170 is shown having two triggers 188 and 188' with legs overlying extension 186; however, either trigger can be provided separately depending on the desirability of being responsive to distally-biased movement of the safety shield and/or the penetrating member. Use of the modified safety penetrating instrument is similar to that described above in connection with safety penetrating instruments 20 and 120 with the exception of both the latch spring 172 and latch arm 100 must be disengaged in order for the safety shield 146 to be moved distally to the extended protruding position.

Figure 5:
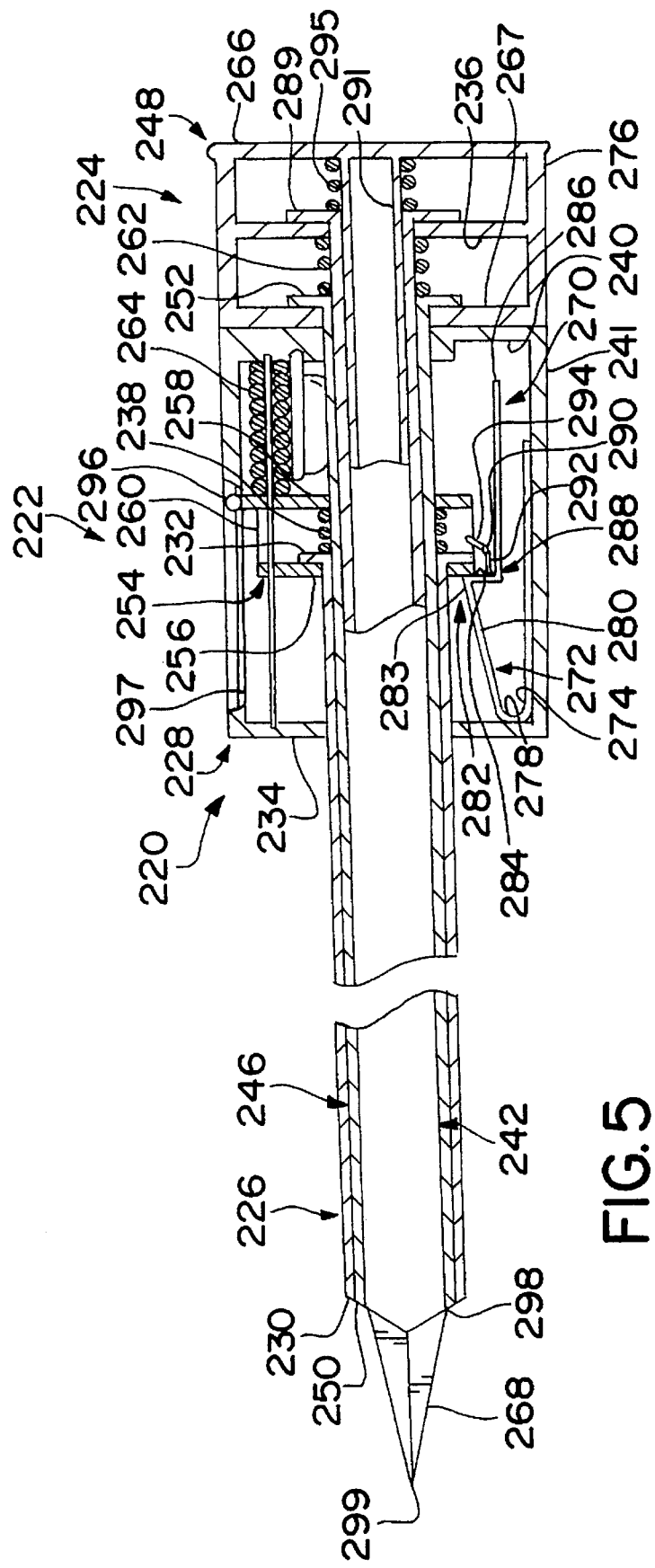
FIG. 5 is a broken side view, partly in section, of another modification of the safety penetrating instrument according to the present invention.

A further modification of the safety penetrating instrument of the present invention is shown in FIG. 5 at 220 wherein movement of the portal sleeve to an extended protruding position is triggered by distally-biased movement of the portal sleeve in response to a reduction in force from tissue contact following entry into the anatomical cavity. The modified safety penetrating instrument 220 includes a portal unit 222 and a penetrating unit 224. Portal unit 222 includes a portal sleeve 226 similar to portal sleeve 26 but with portal sleeve flange 232 mounted within a rail member 254 movably disposed within housing 228. Rail member 254 is similar to rail member 54 and is generally U-shaped including a forward wall 256 disposed transverse or perpendicular to a longitudinal axis of the penetrating instrument, a rearward wall 258 in configuration parallel to forward wall 256 and a sidewall 260 transversely joining the forward and rearward rail member walls. Portal sleeve flange 232 is disposed between the rail member forward and rearward walls with the rail member forward wall 256 having an opening therein allowing passage therethrough by the portal sleeve 226. The rail member forward and rearward walls are disposed parallel or substantially parallel to portal sleeve flange 232, and a bias member 238, similar to bias member 38, is connected between portal sleeve flange 232 and the rail member rearward wall 258 to bias the portal sleeve distally. As shown, bias member 238 includes a helical coil spring disposed around the safety shield 246 and mounted in compression between portal sleeve flange 232 and the rail member rearward wall 258 to bias the portal sleeve 226 distally.

An extending member 264 is similar to extending member 64 but is mounted between rail member rearward wall 258 and a rear wall 240 of housing 228 to bias the portal sleeve 226 in a distal direction to an extended protruding position where distal end 230 of the portal sleeve is disposed beyond the sharp tip 299 of the penetrating member 242. As shown, the extending member includes a helical coil spring disposed around the safety shield 246 and mounted in compression between the rail member rearward wall 258 and the housing rearward wall 240.

A locking and releasing mechanism 270, similar to locking and releasing mechanism 70 but mounted within housing 228, locks the portal sleeve in a retracted position, shown in FIG. 5, exposing the penetrating member distal end 268 and also functions to release the rail member 254 allowing the portal sleeve 226 to move to the extended protruding position. The locking and releasing mechanism 270 includes a latch or locking spring 272, made of a strip of resilient material, formed to have a substantially flat base 274 secured to a bottom wall 241 of housing 228 and a bend 278 joining the base 274 with an upwardly angled arm 280 spaced from the base. Arm 280 carries or forms a latch 282 having a distally angled latching surface joining a proximal latching surface 284 disposed substantially transverse to the longitudinal axis of the safety penetrating instrument and substantially parallel to the rail member forward wall 256. Arm 280 has an extension 286 positioned proximally of latch 282, and a releasing member or trigger 288 is juxtaposed with extension 286. The trigger 288 is pivotally mounted in the housing on a pin 290 secured to a wall or walls of the housing or a structure supported in the housing, and the trigger is generally L-shaped with a leg 292 overlying extension 286 and a leg 294 extending transversely from leg 292 but at a slight angle toward the proximal end of the safety penetrating instrument. A torsion spring (not shown) is coiled around pin 290 and fixed to trigger 288 to bias the trigger counterclockwise.

A handle 296 can be coupled with the portal sleeve 226, such as with flange 232 or rail member 254, for movement along a slot 297 formed in the housing 228 to move the portal sleeve from the extended protruding position to the locked retracted position.

Penetrating unit 224 includes a hub 248 mounting the proximal ends of a penetrating member 242 and a safety shield 246. Safety shield 246 is similar to safety shield 46 and includes a distal end 250 and a proximal flange 252; however, safety shield flange 252 is disposed between a front wall 267 of the hub and a transverse wall or partition 236, proximally spaced from front wall 267, rather than between the walls of a rail member. A bias member 262, similar to bias member 62, is held in compression between the safety shield flange 252 and the transverse wall 236 to distally bias the safety shield 246 while permitting proximal movement thereof away from a rest position where the safety shield flange 252 abuts the front wall 267. Transverse wall 236 also serves as a stop or abutment limiting distal movement of the penetrating member flange 289.

In use, safety penetrating instrument 220 will normally be provided with the portal sleeve 226 in the extended position where the distal end 230 of the portal sleeve protrudes beyond the penetrating member distal end 268. Penetrating member 242 is provided in a rest position where the penetrating member flange 289 abuts the stop formed by wall 236 under the influence of bias member 195. Additionally, the safety shield 246 is provided in a rest position where a distal end 250 of the safety shield is aligned with the penetrating member transverse dimensional transition 298 and the safety shield flange 252 abuts the hub front wall 267.

Prior to commencing penetration of an anatomical cavity wall, handle 296 is grasped and manually moved proximally to move portal sleeve 226 proximally against the bias of extending member 264 until rail member forward wall 256 rides over latch 282 by engaging the angled distal latching surface of the latch to move arm 280 towards base 274. When rail member forward wall 256 moves proximally past the proximal latching surface 284, latching arm 280 springs back to lock the rail member 254 and portal sleeve 226 in the retracted position. With the portal sleeve 226 locked in the retracted position, the distal end 230 of the portal sleeve will be disposed adjacent the transverse dimensional transition 298 of the penetrating member 242 and the safety shield distal end 250.

When penetration of the anatomical cavity wall is commenced, the force from tissue contact on the portal sleeve, penetrating member and safety shield distal ends 230, 268 and 250 will cause the portal sleeve, penetrating member and safety shield to move together proximally against the bias of springs 238, 295 and 262, respectively. Proximal movement of the portal sleeve 226 causes portal sleeve flange 232 to move past trigger leg 294. Movement of flange 232 proximally past trigger leg 294 does not cause movement of latch 282 and, accordingly, the flange 232 is then positioned proximally of the trigger leg 294.

Upon entry into the anatomical cavity, the counterforce on the portal sleeve, penetrating member and safety shield distal ends caused by tissue contact is reduced allowing bias members 238, 295 and 262 to move the portal sleeve, penetrating member and safety shield distally. Distal movement of the portal sleeve causes portal sleeve flange 232 to engage trigger leg 294 and to pivot the trigger counterclockwise looking at FIG. 5 causing leg 292 to engage arm extension 286. Arm 280 is thus moved toward base 274 moving the latch 282 out of engagement with the rail member forward wall 256 and allowing extending member 264 to cause the portal sleeve to move further distally to the extended protruding position wherein the portal sleeve distal end 230 protrudes beyond the distal end 268 of the penetrating member as shown in FIG. 6. The penetrating unit 224 including the penetrating member 242 and the safety shield 246 can then be withdrawn from the portal unit 222 leaving the portal sleeve 226 in place.

The safety penetrating instrument 320 illustrated in FIG. 7 is similar to safety penetrating instrument 220 with the exception that movement of the portal sleeve to the extended protruding position is triggered by distally-biased movement of the safety shield in response to a reduction in force from tissue contact following entry into the anatomical cavity. Safety shield 346 is similar to safety shield 46 but carries a radial protrusion 347 suitably positioned to be disposed within housing 328 when hub 348 is mated with housing 328. Radial protrusion 347 can be a separate member carried on or within the safety shield in a manner to protrude radially therefrom or can be integrally formed as part of the safety shield. The integral protrusion 347 shown is formed using a tongue of material cut from the tubular body of the safety shield and is configured to present a transverse distal abutment surface 349 substantially perpendicular to the longitudinal axis of the safety penetrating instrument and a bend 351 joining the transverse distal abutment surface with an acutely angled proximal abutment surface 353.

Locking and releasing mechanism 370 is the same as locking and releasing mechanism 270 except that trigger 388 is suitably positioned for being engaged by protrusion 347 rather than by the portal sleeve flange 332. As a result, trigger 388 is more proximally spaced from flange 332 when portal sleeve 326 is in the retracted position shown in FIG. 7.

Use of the safety penetrating instrument 320 is similar to that described above for safety penetrating instrument 220 with the exception that safety shield protrusion 347 rather than portal sleeve flange 332 serves as the operating member for engaging the trigger 388. Prior to penetration, the portal sleeve and safety shield are in the positions shown in FIG. 7 with the safety shield protrusion 347 located distally of trigger leg 394. During penetration, the portal sleeve, penetrating member and safety shield are moved proximally due to the force from tissue contact on the portal sleeve, penetrating member and safety shield distal ends and the safety shield protrusion 347 is moved proximally with the safety shield past trigger leg 394 causing trigger 388 to rotate clockwise looking at FIG. 7. Clockwise rotation of the trigger 388 moves trigger leg 392 away from extension 386 and thus does not release latch 382 holding rail member forward wall 356. Upon penetration into an anatomical cavity, the counterforce on the distal end of the safety shield will be reduced allowing spring 362 to move the safety shield distally causing the vertical abutment surface 349 of the safety shield protrusion 347 to engage trigger leg 394, rotating the trigger 388 counterclockwise. Counterclockwise rotation of trigger 388 causes leg 392 to bear against extension 386 moving latch 382 away from rail member forward wall 356 to release the rail member, thereby allowing extending member 364 to move the rail member and the portal sleeve carried therein distally from the retracted position to an extended protruding position beyond the penetrating member distal tip 399 as shown previously in FIG. 6.

Another modification of the safety penetrating instrument of the present invention is arrived at by combining the locking and releasing mechanisms of safety penetrating instruments 220 and 320 to permit movement of the portal sleeve to the extended protruding position in response to distally-biased movement of either or both of the portal sleeve and safety shield. The modification involves mounting a second trigger, shown in phantom at 388' in FIG. 7, distally spaced from trigger 388 for being engaged by portal sleeve flange 332. With two triggers having legs overlying extension 386, it will be appreciated that counterclockwise rotation of either trigger will result in latch 382 being moved away from rail member 354 to release the rail member and portal sleeve thereby allowing extending member 364 to move the portal sleeve distally to the extended protruding position in response to distally-biased movement of either the portal sleeve or the safety shield.

Figure 8:
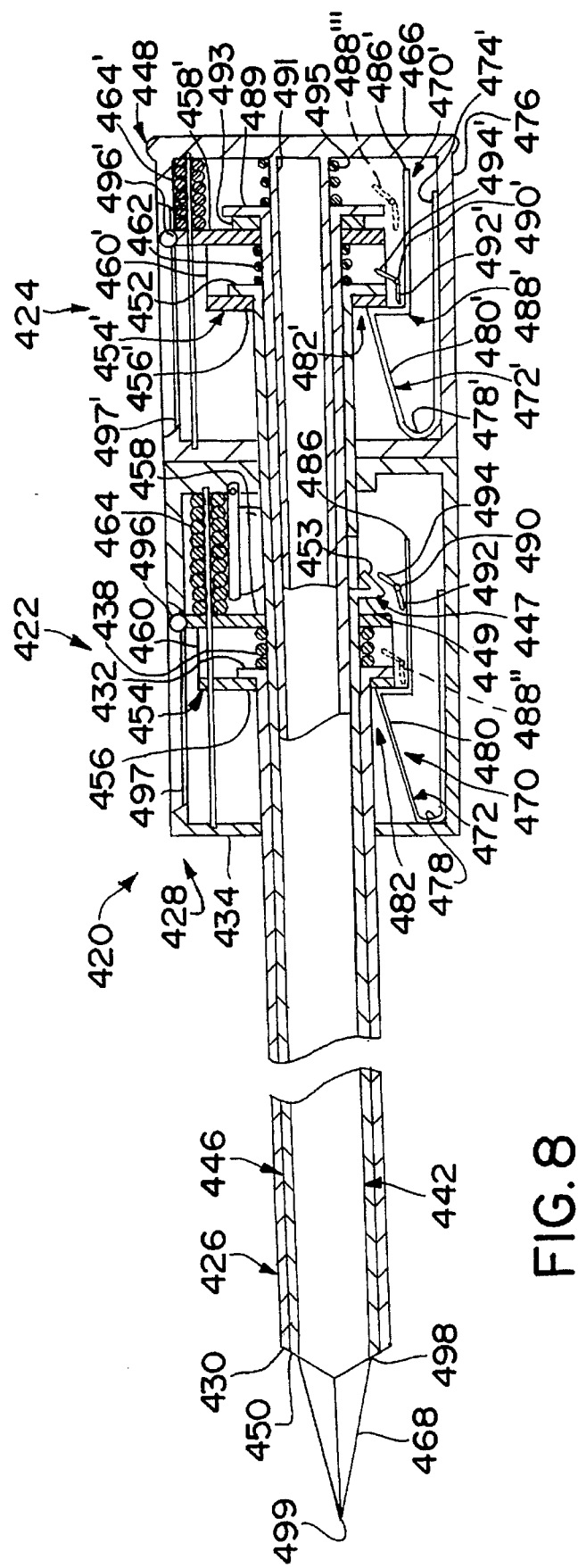
FIG. 8 is a broken side view, partly in section, of another modification of the safety penetrating instrument of the present invention.

Yet another modification of the safety penetrating instrument of the present invention is illustrated in FIG. 8 wherein the modified safety penetrating instrument 420 is similar to safety penetrating instrument 320 with the exception that both the portal sleeve and safety shield are triggered to move distally from retracted positions exposing the penetrating member distal end to extended protruding positions beyond the distal tip of the penetrating member in response to distally-biased movement of the safety shield upon penetrating into an anatomical cavity. Safety penetrating instrument 420 includes a portal unit 422 similar to portal unit 322 for safety penetrating instrument 320 and a penetrating unit 424 similar to penetrating unit 24 for safety penetrating instrument 20. Additionally, safety shield 446 includes a radial protrusion 447 like radial protrusion 347 for safety penetrating instrument 320.

Locking and releasing mechanism 470 for safety penetrating instrument 420 is mounted within housing 428 for engaging the portal sleeve rail member 454 and a similar locking and releasing mechanism 470' is mounted within the hub 448 for engaging the safety shield rail member 454'. Similarly, a pair of extending members 464 and 464' are held in compression between rail member rearward walls 458 and 458' and the rear walls 440 and 466 of the housing and hub, respectively. Bias members 438, 495 and 462 for the portal sleeve, penetrating member and safety shield, respectively, are mounted between respective proximal flanges of the portal sleeve, penetrating member and safety shield and their rail members or the hub rear wall allowing the portal sleeve, penetrating member and safety shield to move proximally during penetration; however, it is distally-biased movement of the safety shield that causes protrusion 447 and safety shield flange 452 to engage triggers 488 and 488' thereby releasing rail members 454 and 454' to be moved distally to extended positions.

Use of the safety penetrating instrument 420 proceeds essentially in the same manner as previously described with the exception that both the portal sleeve and safety shield must be retracted prior to use in order to expose the penetrating member distal end. Handles 496 and 496' are coupled with the portal sleeve and safety shield, respectively, for this purpose and can be grasped and moved proximally together or individually to move the portal sleeve and safety shield from their extended positions shown in FIG. 9 to the retracted position shown in FIG. 8. Once safety shield and portal sleeve rail members have been locked, penetration of the anatomical cavity wall can be commenced as described previously.

Further modifications of the safety penetrating instrument 420 can be arrived at by adding one or both of the triggers shown in phantom at 488" and 488'" in FIG. 8 to make use of the portal sleeve flange 432 and/or the penetrating member flange 489 as operating members together with the safety shield protrusion 447 and flange 452.

Figures 9, 10:
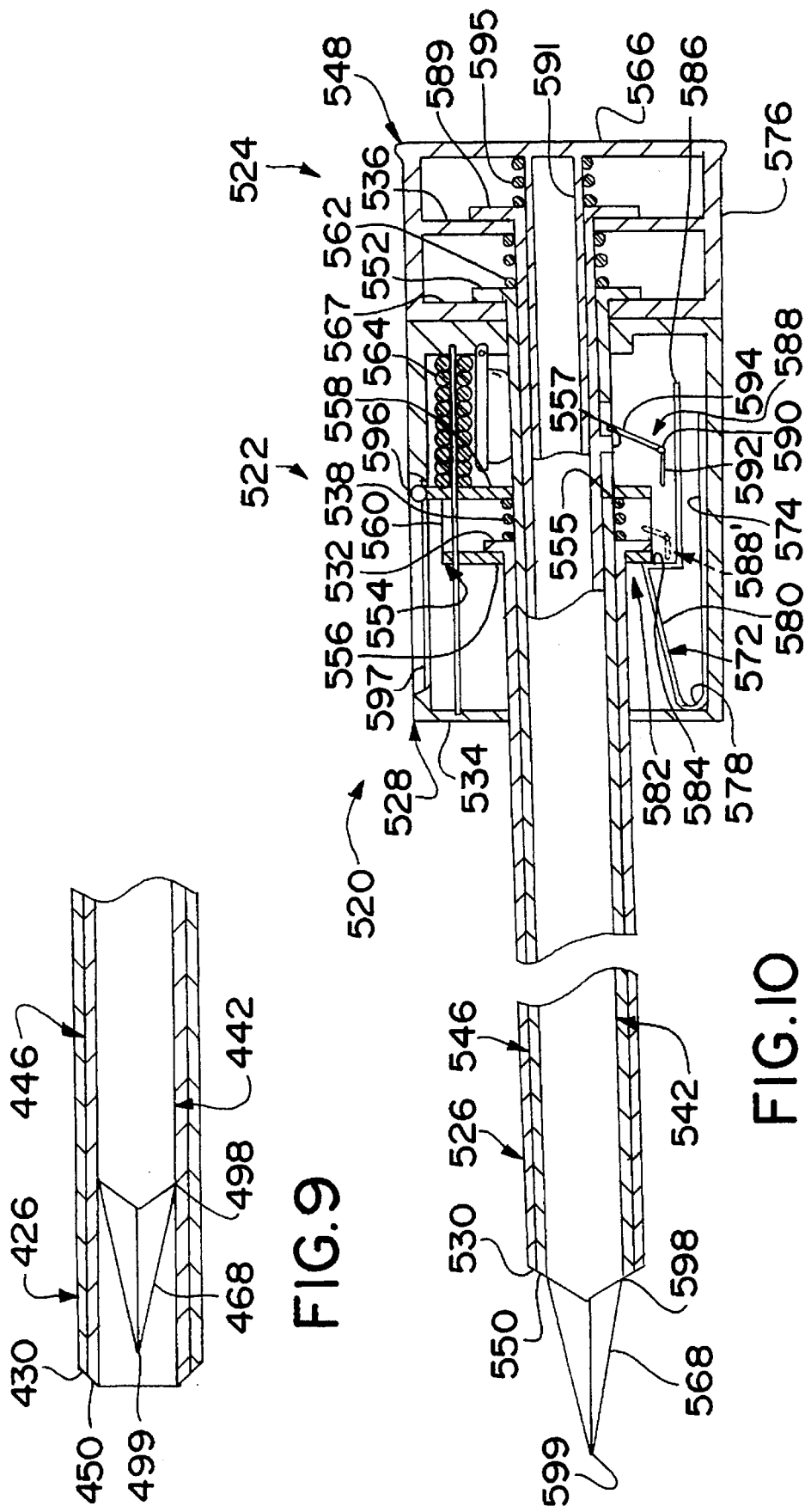
FIG. 9 is a side view, partly in section, of the distal end of the safety penetrating instrument of FIG. 8 following penetration into the anatomical cavity.
FIG. 10 is a broken side view, partly in section, illustrating yet another modification of the safety penetrating instrument of the present invention.

The modified safety penetrating instrument illustrated in FIG. 10 at 520 is similar to safety penetrating instrument 320 with the exception of the portal sleeve being triggered to move distally from the retracted position exposing the penetrating member distal end to the extended protruding position beyond the distal end of the penetrating member in response to distally-biased movement of the penetrating member following penetration into the anatomical cavity.

Portal unit 522 and penetrating unit 524 for safety penetrating instrument 520 are essentially the same as portal unit 322 and penetrating unit 324 for safety penetrating unit 320; however, safety shield 546 is slotted at 555 and penetrating member 542 carries a radial protrusion 557 extending through the slot 555 into housing 528. Slot 555 extends along a longitudinal axis of the safety shield 546 and is sufficiently long to permit the radial protrusion 557 to move along the slot without obstruction when the penetrating member 542 and safety shield 546 move relative to one another. When penetrating member 542 is in the rest position shown in FIG. 10, the penetrating member flange 589 abuts transverse wall 536 and radial protrusion 557 is located distally of trigger leg 594. Proximal movement of penetrating member 542 caused by tissue resistance during penetration moves protrusion 557 proximally along slot 555 and past trigger leg 594. Upon penetrating into the anatomical cavity, the force from tissue contact is reduced allowing bias member 595 to move the penetrating member 542 distally. Protrusion 557 is carried along with penetrating member 542 in a distal direction and engages leg 594 to rotate the trigger 588 counterclockwise. Latch 582 is thus released from the rail member forward wall 556 allowing extending member 564 to move the portal sleeve to the extended protruding position previously shown in FIG. 6.

Another modification of the safety penetrating instrument of the present invention is arrived at by mounting a second trigger, shown in phantom at 588' in FIG. 10, distally spaced from trigger 588 for being engaged by the portal sleeve flange 532. With two triggers having legs overlying extension 586, counterclockwise rotation of either trigger will result in latch 582 being moved away from rail member 554 to release the rail member and portal sleeve thereby allowing extending member 564 to move the portal sleeve distally to the extended protruding position in response to distally-biased movement of either the portal sleeve or the penetrating member.

Still another modification of the safety penetrating instrument according to the present invention is arrived at by use of the modified hub shown in FIG. 11 with any of the housings shown in FIGS. 5, 7 and 10. The modified hub 648 is similar to those previously described but with the safety shield 646 telescopically fitted over the penetrating member 642 in nesting relation such that the penetrating member flange 689 abuts the safety shield flange 652 when the penetrating member and safety shield are in rest positions against the front wall 667 of the hub. Bias member 695 for hub 648 is disposed around guide tube 691 and held in compression between the penetrating member flange 689 and the rear wall 666 of the hub to bias the penetrating member flange and thus the safety shield flange distally toward the front wall of the hub. As a result, proximal movement of the safety shield will tend to drive the penetrating member and distally-biased movement of penetrating member will tend to drive the safety shield such that any radial protrusions carried by one or both members are also driven, triggering release of the portal sleeve to move to the extended protruding position in response to distally-biased movement of both the penetrating member and safety shield.

Yet another modification of the safety penetrating instrument of the present invention is illustrated in FIG. 12 wherein the modified safety penetrating instrument 720 is similar to safety penetrating instrument 420 with the exception that both the portal sleeve and safety shield are triggered to move distally from retracted positions exposing the penetrating member distal end to extended protruding positions beyond the distal tip of the penetrating member in response to distally-biased movement of the penetrating member upon penetrating into an anatomical cavity. Safety penetrating instrument 720 includes a portal unit 722 similar to portal unit 422 for safety penetrating instrument 420 and a penetrating unit 724 similar to penetrating unit 424 for safety penetrating instrument 420. However, in safety penetrating instrument 720, penetrating member 742 includes a radial protrusion 757 like radial protrusion 557 for safety penetrating instrument 520.

Locking and releasing mechanism 770 for safety penetrating instrument 720 is mounted within housing 728 for engaging the portal sleeve rail member 754 and a similar locking and releasing mechanism 770' is mounted within the hub 748 for engaging the safety shield rail member 754'. Similarly, an extending member 764 is held in compression between the portal sleeve rail member rearward wall 758 and the housing rear wall 740, and another extending member 764' is held in compression between the safety shield rail member rearward wall 758' and the rear wall 766 of the hub. Upon penetrating into an anatomical cavity, distally-biased movement of the penetrating member 742 causes protrusion 757 and penetrating member flange 789 to engage triggers 788 and 788', respectively, thereby releasing the portal sleeve and safety shield to be moved distally to extended positions.

Use of the safety penetrating instrument 720 proceeds essentially as previously described with the exception that both the portal sleeve and safety shield must be retracted prior to use in order to expose the penetrating member distal end 768. Handles 796 and 796' are coupled with the portal sleeve and safety shield, respectively, for this purpose and can be grasped and moved proximally together or individually to move the portal sleeve and/or safety shield from the extended positions shown in FIG. 9 to the retracted positions shown in FIG. 12. Once the safety shield rail member 754 and portal sleeve rail member 754' have been locked in retracted positions, penetration of the anatomical cavity wall W can be commenced as previously described.

Other modifications of the safety penetrating instrument of the present invention are arrived at by mounting one or both of third and fourth triggers, shown in phantom at 788" and 788'" in FIG. 12, distally spaced from triggers 788 and 788', respectively, for being engaged by the portal sleeve flange 732 and safety shield flange 752. Depending on the number and placement of the additional triggers, both the safety shield and portal sleeve can be moved to extended protruding positions protecting the distal end of the penetrating member in response to distally-biased movement of any combination of the penetrating member, safety shield and portal sleeve upon penetrating into the anatomical cavity. Also in FIG. 12, a second slot 785 is formed in safety shield 746 distally of slot 755 such that a strip or band of material 747 separates the slots. Band 747, like the safety shield protrusion 447, can function as an operating member. A fifth trigger, shown in phantom at 787 in FIG. 12, can be positioned above arm extension 786 to be engaged by the safety shield band 747 and to trigger release of latch 782.

In the embodiments shown, the respective distal ends of the cannula and of the safety shield or probe are aligned with a transverse dimensional transition or junction joining the cylindrical shaft of the penetrating member with the penetrating member distal end immediately prior to use in penetrating the anatomical cavity wall; and since the penetrating member, portal sleeve and safety shield are all movable during penetration, the distal ends of the portal sleeve and safety shield tend to remain aligned with the junction and to become displaced proximally relative to the housing and hub, with at least one of the penetrating member, portal sleeve and safety shield triggering protrusion of a safety member (i.e., the cannula and/or the safety shield or probe) when biased to move distally upon entering the anatomical cavity.

FIG. 13 shows an alternative distal configuration or alignment for the safety penetrating instruments of the present invention prior to penetration wherein the distal ends 30 and 50 of the portal sleeve and safety shield 26 and 46 are spaced distally of the penetrating member junction 98 a predetermined distance x. In this configuration, the portal sleeve and safety shield will move proximally during penetration towards becoming aligned with the junction of the penetrating member and will move together with the penetrating member to ease penetration by maintaining a smooth profile. The penetrating member, safety shield and portal sleeve will spring back toward the position shown in FIG. 13 upon entering into the anatomical cavity with at least one of the penetrating member, safety shield and portal sleeve triggering further distal movement or protrusion beyond the penetrating member distal end by the portal sleeve and/or the safety shield.

FIG. 14 shows an alternative distal configuration for the safety penetrating instruments of the present invention wherein the distal end 30 of the portal sleeve 26 is spaced distally from the penetrating member distal end junction 98 prior to use and the safety shield distal end 50 is spaced proximally of the portal sleeve distal end a predetermined distance x. In this configuration, the portal sleeve distal end will move proximally during penetration towards becoming aligned with the penetrating member distal end junction and will move proximally with the penetrating member distal end towards becoming aligned with the safety shield distal end. The portal sleeve, penetrating member and safety shield will spring back towards the original positions shown in FIG. 14 upon entering into the anatomical cavity with at least one of the members triggering protrusion beyond the penetrating member distal end 68 by the portal sleeve and/or the safety shield.

Another alternative distal configuration for the safety penetrating instruments of the present invention is shown in FIG. 15 wherein the distal end 50 of the safety shield 46 is aligned with the penetrating member distal end junction 98 prior to use and the distal end 30 of the portal sleeve 26 is spaced distally of the safety shield distal end 50 a predetermined distance x. In this configuration, the portal sleeve distal end will move proximally toward being aligned with the penetrating member and safety shield distal ends during penetration and will move together with the penetrating member and safety shield to maintain alignment. The portal sleeve, penetrating member and safety shield will spring back distally upon entering the anatomical cavity with at least one of the members triggering further distal movement or protrusion of the portal sleeve and/or the safety shield.

Yet another distal configuration for safety penetrating instruments of the present invention is shown in FIG. 16 wherein the distal end 30 of the portal sleeve 26 is aligned with the penetrating member distal end junction 98 prior to use and the safety shield distal end 50 is spaced distally of the portal sleeve distal end 30 a predetermined distance x. In this configuration, the safety shield distal end will move proximally during penetration towards becoming aligned with the portal sleeve distal end and will move further proximally along with the portal sleeve and penetrating member during penetration. Upon entering into the anatomical cavity, the portal sleeve, penetrating member and safety shield will spring back towards the original positions shown with at least one of the members triggering protrusion beyond the penetrating member distal end by the portal sleeve and/or the safety shield.

Another distal configuration for the safety penetrating instruments of the present invention is shown in FIG. 17 wherein the distal end 50 of the safety shield 46 is distally spaced from the penetrating member distal end junction 98 a predetermined distance x and the portal sleeve distal end 30 is proximally spaced from the penetrating member distal end junction 98 a predetermined distance y. In this configuration the safety shield will move proximally during penetration towards becoming aligned with the penetrating member distal end junction and will move together with the penetrating member into alignment with the portal sleeve to ease penetration. Upon entering into the anatomical cavity, the portal sleeve, penetrating member and safety shield will spring back towards the original position shown thereby triggering protrusion beyond the penetrating member distal end by the portal sleeve and/or the safety shield.

Still another initial distal configuration for the safety penetrating instruments of the present invention is shown in FIG. 18 wherein the distal end 30 of the portal sleeve 26 is aligned with the penetrating member distal end junction 98 and the safety shield distal end 50 is spaced proximally of the portal sleeve distal end 30 a predetermined distance x. In this configuration, the portal sleeve and penetrating member will move proximally during penetration into alignment with the safety shield and will move further proximally along with the safety shield until penetration of one or more of the members into the anatomical cavity.

Another distal configuration for the safety penetrating instruments of the present invention is shown in FIG. 19 wherein the distal end 50 of the safety shield 46 is aligned with the penetrating member distal end junction 98 prior to use and the distal end 30 of the portal sleeve 26 is spaced proximally of the safety shield distal end 50 a predetermined distance x. In this configuration, the penetrating member and safety shield distal ends will move proximally during penetration towards being aligned with the portal sleeve distal end and will stop or move together with the portal sleeve until penetration of one or more of the members into the anatomical cavity. The portal sleeve, penetrating member and safety shield will spring back distally upon entering the anatomical cavity and at least one of the members will trigger further distal movement or protrusion of the portal sleeve and/or safety shield.

A further distal configuration for safety penetrating instruments of the present invention is shown in FIG. 20 wherein the portal sleeve and safety shield distal ends 30 and 50 are located proximally of the penetrating member distal end junction 98 prior to penetrating the wall of an anatomical cavity. In this configuration, the penetrating member will move proximally during penetration towards becoming aligned with the safety shield and portal sleeve distal ends and will stop or move together with the safety shield and portal sleeve until penetration into the anatomical cavity. The portal sleeve, penetrating member and safety shield will spring back to the original positions upon entering into the anatomical cavity thereby triggering protrusion of the portal sleeve and/or safety shield beyond the penetrating member distal end 68 to function as safety members.

From the above, it will be appreciated that the penetrating member, portal sleeve and safety shield of the safety penetrating instrument of the present invention are movable proximally during penetration of an anatomical cavity wall and distally upon entering the anatomical cavity to trigger further distal movement or protrusion of the portal sleeve and/or safety shield to function as safety members protecting the distal end of the penetrating member. By "safety member" is meant any structure moveable distally relative to the penetrating member to protect the tip of the penetrating member within an anatomical cavity. Since in the safety penetrating instrument of the present invention one or both of the portal sleeve and safety shield can be extended to protect the penetrating member tip, each can function as a safety member upon penetration of the safety penetrating instrument into an anatomical cavity. The cannula, whether or not it functions as a safety member, can be a portal sleeve, a needle open at both ends with fluid flow therethrough, a catheter or any other tubular component of a medical instrument. When the cannula is not triggered to protrude as a safety member, it is coupled with a safety member such as a tubular safety shield disposed between the cannula and a penetrating member, a safety probe fitted within a hollow penetrating member, or a component partly within and around the penetrating member and movable distally to protrude relative to the penetrating member to protect the distal end thereof when triggered. On the other hand, if the cannula does function as a safety member, it can be coupled with a protective sheath or probe that is not triggered to protrude or with any of the aforementioned safety members. Additionally, the triggered safety member protrusion can be combined with penetrating member retraction to provide separate modes of safety.

The components of the safety penetrating instrument of the present invention can be made of any suitable, medical grade materials to permit sterilization for re-use or for single patient use. The components can be made of multiple parts of various configurations and materials to reduce cost. The portal unit can have various valves, stop cocks and seals in the housing to control fluid flow therethrough, and conventional detent mechanisms can be used to connect or latch the hub with the housing when the portal unit and the penetrating unit are assembled. The distal ends of the cannula and the safety shield can be chamfered or blunt, smooth or roughened, or have any other configuration depending on the need for ease of penetration or increased resistance. Further, the safety shield can be mounted either by the portal unit or the penetrating unit depending on the desirability of being left in place within the portal sleeve or withdrawn with the penetrating member.

Figure 26:
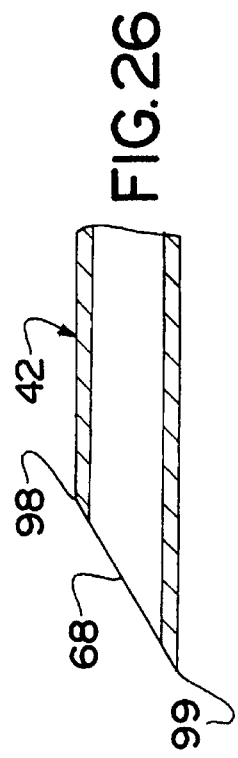
FIGS. 21–26 are side views of alternative distal configurations for the penetrating member of the safety penetrating instrument of the present invention.
Figure 21:
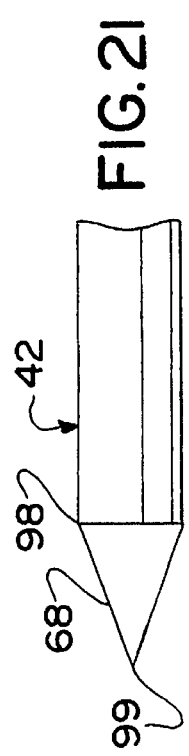
Figure 22:
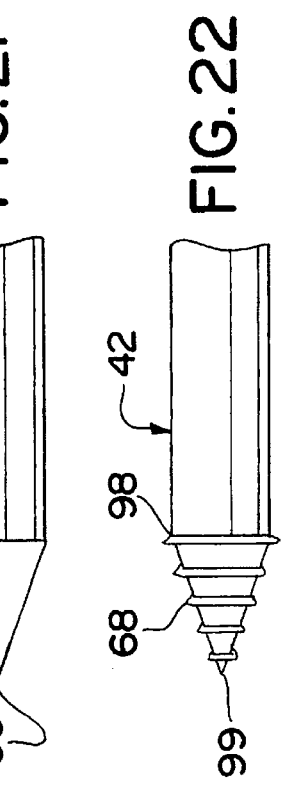
Figure 23:
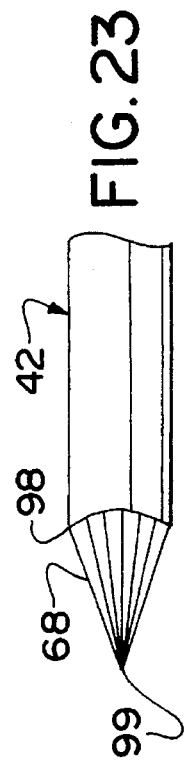
Figure 24:
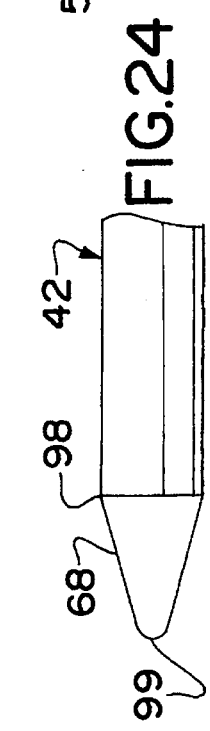
Figure 25:
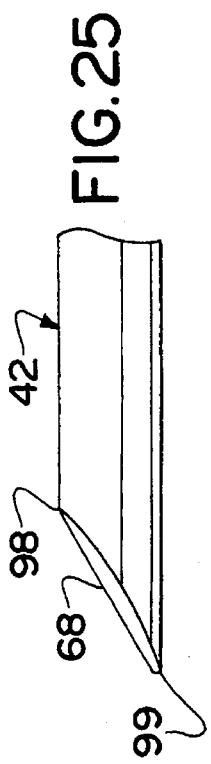

The penetrating member can be solid, hollow or partially solid and hollow, formed as single or multiple pieces, and fixed as shown or movable telescopically over a guide tube or the like. The distal end 68 of the penetrating member 42 can have any configuration desired for a particular procedure, for example, the pyramidal trocar configuration shown or a conical distal end (FIG. 21), a threaded distal end (FIG. 22), a multifaceted distal end (i.e., having two or more facets as shown in FIG. 23), a blunt distal end (FIG. 24), a slanted distal end (FIG. 25) or a hollow needle configuration with fluid flow therethrough (FIG. 26). Additionally, the surface defining the distal end of the penetrating member can be irregular or smooth, continuous or perforated, provided with cutting features or having any combination of the above. If the penetrating member 42 is a hollow needle having a beveled distal end 68 as shown or a curved Tuohey-type distal configuration, the proximal edge of the opening at the distal end of the needle is considered the transverse dimensional transition or junction 98 and thus the cannula and/or safety shield distal end is aligned with the distal end of the needle when located adjacent the proximal edge. It will also be appreciated that when the penetrating member is a hollow needle, the proximal end of the needle can be connected with various valves for regulating fluid flow through the needle.

Figure 27:
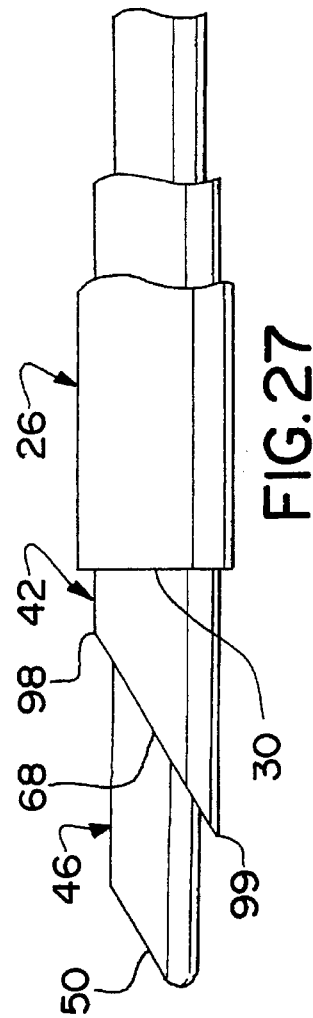
FIG. 27 is a side view, partly in section, of the distal end of a penetrating member configured to accommodate a safety probe.

As mentioned previously, the safety member of the present invention can be a tubular member such as a cannula or a safety shield disposed between a cannula and penetrating member, or in the case of a hollow penetrating member, the safety member can be a probe disposed at least partially within the penetrating member and movable through one or more apertures formed at or near the distal end of the penetrating member. FIG. 27 shows a cannula 26 surrounding a hollow penetrating member 42 with a beveled distal opening and a cylindrical safety probe 46 in an extended protruding position to protect the distal end 68 of the penetrating member. The safety probe has a beveled distal end 50 and is preferably movable from the extended position shown to a retracted position where the beveled distal end of the safety probe is flush with the distal end of the penetrating member. It will be appreciated that a coaxial extending mechanism can be fitted within the penetrating member to move the safety probe to the extended position or a flange can be carried at the safety probe proximal end and passed through a slot or opening in the penetrating member to be acted on by any of the extending mechanisms previously described. The safety probe distal end can have any configuration to protrude through single or multiple openings formed in the penetrating member distal end and can conform to the distal profile of the penetrating member or present a discontinuous surface when retracted.

The rail member can have various configurations to engage the latch and be released by the trigger. Preferably, the rail member will have a configuration to serve as a stop or abutment for the operating member as exemplified herein by a U-shaped rail member.

The locking and releasing mechanisms require only a latch for locking the safety member in the retracted position and a trigger for releasing the latch in response to distal movement of an operating member; and, thus, it will be appreciated that various mechanisms can be employed to produce the locking and releasing functions such as, for example, multiple movably or pivotally mounted cams or pawls. It will be appreciated that the locking and releasing mechanism can be designed and arranged in the housing or the hub in various ways to minimize the length of the housing or the hub and, therefore, the overall length of the housing and hub. Various locking and releasing mechanisms that can be simply modified for use in the safety penetrating instrument of the present invention are disclosed in Applicant's pending applications Ser. No. 07/800,507, filed Nov. 27, 1991, Ser. No. 07/805,506, filed Dec. 6, 1991, Ser. No. 07/808,325, filed Dec. 16, 1991, Ser. No. 07/848,838, filed Mar. 10, 1992, Ser. No. 07/868,566 and Ser. No. 07/868,578, filed Apr. 15, 1992, Ser. No. 07/929,338, filed Aug. 14, 1992, Ser. No. 07/845,177, filed Sep. 15, 1992, Ser. No. 07/945, 177, filed Sep. 15, 1992, Ser. No. 08/079,586, filed Jun. 22, 1993, Ser. No. 08/195,512, filed Feb. 14, 1994, Ser. No.

08/196,029, filed Feb. 14, 1994, Ser. No. 08/196,027, filed Feb. 14, 1994, Ser. No. 08/195,178, filed Feb. 14, 1994, Ser. No. 08/237,734, filed May 4, 1994, Ser. No. 08/247,205, filed May 20, 1994, Ser. No. 08/254,007, filed Jun. 3, 1994 and Ser. No. 08/260,439, filed Jun. 15, 1994, the disclosures of which are incorporated herein by reference. The above applications disclose automatically retracting safety penetrating instruments such that modification of the locking and releasing mechanisms requires configuring the latches to lock a member in a retracted position rather than in an extended position. The above applications also disclose various bias arrangements useful with the safety penetrating instrument of the present invention. Other locking and releasing mechanisms that can be used in the safety penetrating instrument of the present invention are disclosed in Applicant's pending applications Ser. Nos. 08/279,170 and 08/279,172, filed Jul. 22, 1994, the disclosures of which are incorporated herein by reference.

One or more control buttons, such as the control buttons described in Applicant's copending patent application, Ser. No. 08/083,220, filed Jun. 24, 1993, can be mounted next to any latch for manually disengaging the latch to prevent locking of the safety member in the retracted position, in some cases converting the safety penetrating instrument to a standard safety shielded penetrating instrument without triggered protrusion. In addition, any latch or separate spring member can carry a secondary pawl or protrusion at a distal end for locking the safety member in the extended position and can then be released through the use of a control button as described above.

The transverse or radial protrusions carried by the safety shield and/or the penetrating member in some embodiments can be integrally formed on an exterior surface of the safety shield or penetrating member as shown or can be mounted within the safety shield or penetrating member as part of a pivoted lever protruding through slots in the penetrating member and safety shield to engage triggers in respective housings. If part of a pivoted lever, the protrusions can be made to withdraw into their respective safety shields or penetrating member by rotating the lever, for example by use of a control button positioned adjacent the lever and operable to cam the lever in a manner to withdraw the protrusion. The pivoted protrusions described in Applicant's pending patent applications Ser. Nos. 08/279,170 and 08/279,172, filed Jul. 22, 1994, are exemplary of the types of pivoted protrusions that can be used for this purpose.

It will also be appreciated that the safety penetrating instrument of the present invention permits use of strong bias springs to ensure movement of the safety member (whether it be the cannula, a safety shield or probe, or both) to the extended protruding position without increasing the force to penetrate. After penetration of the safety penetrating instrument into the anatomical cavity, the safety member acts as a shock absorber upon inadvertent contact with tissue which contact can be felt by the surgeon and visually determined by movement of the handle. The distal bias for the triggering member (i.e., the cannula and/or safety shield or probe) of the safety penetrating instrument need only be strong enough to allow slight movement of the member during penetration such that the force-to-penetrate can be minimized. The features of the various embodiments described above can be combined in any manner desired dependent upon the requirements and complexity of the safety penetrating instrument.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A safety penetrating instrument for establishing a portal in the wall of an anatomical cavity comprising a housing;

an elongate cannula mounted by said housing and having a distal end for being introduced into the anatomical cavity and a proximal end for positioning externally of the anatomical cavity;

a penetrating member disposed in said cannula and having a distal end for penetrating the anatomical cavity wall, said penetrating member being movable relative to said housing between an extended rest position and a penetrating member retracted position;

a safety member disposed in said cannula and having a distal end, said safety member being movable relative to said housing between a safety member extended position where said safety member distal end protrudes distally from said penetrating member distal end and a safety member retracted position where said safety member distal end is disposed proximally of said penetrating member distal end to expose said penetrating member distal end;

safety member extending means for moving said safety member distally relative to said housing from said safety member retracted position to said safety member extended position;

means for manually moving said safety member proximally relative to said housing from said safety member extended position to said safety member retracted position;

safety member locking means for locking said safety member in said safety member retracted position to prevent distal movement of said safety member relative to said housing beyond said safety member retracted position while permitting proximal movement of said safety member relative to said housing during penetration of the anatomical cavity wall;

safety member bias means for biasing said safety member distally relative to said housing in said safety member retracted position while permitting said safety member to move proximally relative to said housing from said safety member retracted position during penetration of the anatomical cavity wall and distally toward said safety member retracted position following entry into the anatomical cavity;

cannula bias means for biasing said cannula distally relative to said housing toward a cannula rest position and for permitting proximal movement of said cannula relative to said housing during penetration of the anatomical cavity wall;

penetrating member bias means for biasing said penetrating member distally relative to said housing toward said penetrating member rest position and for permitting proximal movement of said penetrating member relative to said housing during penetration of the anatomical cavity wall; and releasing means responsive to penetration of said safety penetrating instrument into the anatomical cavity for triggering release of said safety member locking means to permit said safety member extending means to move said safety member distally relative to said housing from said safety member retracted position to said safety member extended position.

2. A safety penetrating instrument as recited in claim 1 wherein said safety member is a tubular safety shield disposed between said penetrating member and said cannula.

3. A safety penetrating instrument as recited in claim 1 wherein said penetrating member is at least partly hollow and said safety member is a safety probe disposed within said penetrating member.

4. A safety penetrating instrument as recited in claim 1 wherein said releasing means is responsive to distally-biased movement of said safety member upon penetrating into the anatomical cavity.

5. A safety penetrating instrument as recited in claim 1 wherein said releasing means is responsive to distally-biased movement of said penetrating member upon penetrating into the anatomical cavity.

6. A safety penetrating instrument as recited in claim 1 wherein said releasing means is responsive to distally-biased movement of said cannula upon penetrating into the anatomical cavity.

7. A safety penetrating instrument as recited in claim 1 wherein said releasing means is responsive to distally-biased movement of said safety member and said penetrating member upon penetrating into the anatomical cavity.

8. A safety penetrating instrument as recited in claim 1 wherein said releasing means is responsive to distally-biased movement of said safety member and said cannula upon penetrating into the anatomical cavity.

9. A safety penetrating instrument as recited in claim 1 wherein said releasing means is responsive to distally-biased movement of said cannula and said penetrating member upon penetrating into the anatomical cavity.

10. A safety penetrating instrument as recited in claim 1 wherein said releasing means is responsive to distally-biased movement of said safety member, said cannula and said penetrating member upon penetrating into the anatomical cavity.

11. A safety penetrating instrument as recited in claim 1 wherein said penetrating member distal end extends distally from a transverse dimensional transition in said penetrating member and said safety member distal end is aligned with said transition when in said retracted position.

12. A safety penetrating instrument as recited in claim 11 wherein said cannula distal end is aligned with said safety member distal end when said cannula is in said rest position and said safety member is in said retracted position.

13. A safety penetrating instrument as recited in claim 11 wherein said cannula distal end is spaced proximally of said safety member distal end when said cannula is in said rest position and said safety member is in said retracted position.

14. A safety penetrating instrument as recited in claim 11 wherein said cannula distal end is spaced distally of said safety member distal end when said cannula is in said rest position and said safety member is in said retracted position.

15. A safety penetrating instrument as recited in claim 1 wherein said penetrating member distal end extends distally from a transverse dimensional transition in said penetrating member and said safety member distal end is located proximally of said transition when in said retracted position.

16. A safety penetrating instrument as recited in claim 15 wherein said cannula distal end is aligned with said safety member distal end when said cannula is in said rest position and said safety member is in said retracted position.

17. A safety penetrating instrument as recited in claim 15 wherein said cannula distal end is spaced proximally of said safety member distal end when said cannula is in said rest position and said safety member is in said retracted position.

18. A safety penetrating instrument as recited in claim 15 wherein said cannula distal end is spaced distally of said safety member distal end when said cannula is in said rest position and said safety member is in said retracted position.

19. A safety penetrating instrument as recited in claim 1 wherein said penetrating member distal end extends distally from a transverse dimensional transition in said penetrating member and said safety member distal end is located distally of said transition when in said retracted position.

20. A safety penetrating instrument as recited in claim 19 wherein said cannula distal end is aligned with said safety member distal end when said cannula is in said rest position and said safety member is in said retracted position.

21. A safety penetrating instrument as recited in claim 19 wherein said cannula distal end is spaced proximally of said safety member distal end when said cannula is in said rest position and said safety member is in said retracted position.

22. A safety penetrating instrument as recited in claim 19 wherein said cannula distal end is spaced distally of said safety member distal end when said cannula is in said rest position and said safety member is in said retracted position.

23. A safety penetrating instrument for establishing a portal in the wall of an anatomical cavity comprising a housing;

an elongate cannula mounted by said housing and having a distal end for being introduced into the anatomical cavity and a proximal end for positioning externally of the anatomical cavity;

a penetrating member disposed in said cannula and having a distal end for penetrating the anatomical cavity wall;

a safety member disposed in said cannula and having a distal end, said safety member being movable relative to said housing between a safety member rest position where said safety member distal end protrudes distally from said penetrating member distal end and a safety member retracted position where said safety member distal end is disposed proximally of said penetrating member distal end to expose said penetrating member distal end;

cannula extending means for moving said cannula distally relative to said housing from a cannula retracted position where said cannula distal end is disposed proximally of said penetrating member distal end to a cannula extended position where said cannula distal end protrudes distally from said penetrating member distal end;

means for manually moving said cannula proximally relative to said housing from said cannula extended position to said cannula retracted position;

cannula locking means for locking said cannula in said cannula retracted position to prevent distal movement of said cannula relative to said housing beyond said cannula retracted position while permitting proximal movement of said cannula during penetration of the anatomical cavity wall;

cannula bias means for biasing said cannula distally relative to said housing when said cannula is in said retracted position and for permitting said cannula to move proximally away from said retracted position during penetration of the anatomical cavity wall;

penetrating member bias means for biasing said penetrating member distally relative to said housing toward a penetrating member rest position and for permitting proximal movement of said penetrating member relative to said housing during penetration of the anatomical cavity wall;

safety member bias means for biasing said safety member distally relative to said housing toward said safety member rest position and for permitting proximal movement of said safety member relative to said housing during penetration of the anatomical cavity wall; and releasing means responsive to penetration of said safety penetrating instrument into the anatomical cavity for triggering release of said cannula locking means to permit said cannula extending means to move said cannula distally relative to said housing from said cannula retracted position to said cannula extended position.

24. A safety penetrating instrument as recited in claim 23 wherein said safety member is a tubular safety shield disposed between said penetrating member and said cannula.

25. A safety penetrating instrument as recited in claim 23 wherein said penetrating member is at least partly hollow and said safety member is a safety probe disposed within said penetrating member.

26. A safety penetrating instrument as recited in claim 23 wherein said releasing means is responsive to distally-biased movement of said safety member upon penetrating into the anatomical cavity.

27. A safety penetrating instrument as recited in claim 23 wherein said releasing means is responsive to distally-biased movement of said penetrating member upon penetrating into the anatomical cavity.

28. A safety penetrating instrument as recited in claim 23 wherein said releasing means is responsive to distally-biased movement of said cannula upon penetrating into the anatomical cavity.

29. A safety penetrating instrument as recited in claim 23 wherein said releasing means is responsive to distally-biased movement of said safety member and said penetrating member upon penetrating into the anatomical cavity.

30. A safety penetrating instrument as recited in claim 23 wherein said releasing means is responsive to distally-biased movement of said safety member and said cannula upon penetrating into the anatomical cavity.

31. A safety penetrating instrument as recited in claim 23 wherein said releasing means is responsive to distally-biased movement of said cannula and said penetrating member upon penetrating into the anatomical cavity.

32. A safety penetrating instrument as recited in claim 23 wherein said releasing means is responsive to distally-biased movement of said safety member, said cannula and said penetrating member upon penetrating into the anatomical cavity.

33. A safety penetrating instrument as recited in claim 23 wherein said penetrating member distal end extends distally from a transverse dimensional transition in said penetrating member and said cannula distal end is aligned with said transition when in said retracted position.

34. A safety penetrating instrument as recited in claim 33 wherein said cannula distal end is aligned with said safety member distal end when said safety member is in said rest position and said cannula is in said retracted position.

35. A safety penetrating instrument as recited in claim 33 wherein said cannula distal end is spaced proximally of said safety member distal end when said cannula is in said retracted position and said safety member is in said rest position.

36. A safety penetrating instrument as recited in claim 33 wherein said cannula distal end is spaced distally of said safety member distal end when said cannula is in said retracted position and said safety member is in said rest position.

37. A safety penetrating instrument as recited in claim 23 wherein said penetrating member distal end extends distally from a transverse dimensional transition in said penetrating member and said cannula distal end is located proximally of said transition when in said retracted position.

38. A safety penetrating instrument as recited in claim 37 wherein said cannula distal end is aligned with said safety member distal end when said cannula is in said retracted position and said safety member is in said rest position.

39. A safety penetrating instrument as recited in claim 37 wherein said cannula distal end is spaced proximally of said safety member distal end when said cannula is in said retracted position and said safety member is in said rest position.

40. A safety penetrating instrument as recited in claim 37 wherein said cannula distal end is spaced distally of said safety member distal end when said cannula is in said retracted position and said safety member is in said rest position.

41. A safety penetrating instrument as recited in claim 23 wherein said penetrating member distal end extends distally from a transverse dimensional transition in said penetrating member and said cannula distal end is located distally of said transition when in said retracted position.

42. A safety penetrating instrument as recited in claim 41 wherein said cannula distal end is aligned with said safety member distal end when said cannula is in said retracted position and said safety member is in said rest position.

43. A safety penetrating instrument as recited in claim 41 wherein said cannula distal end is spaced proximally of said safety member distal end when said cannula is in said retracted position and said safety member is in said rest position.

44. A safety penetrating instrument as recited in claim 41 wherein said cannula distal end is spaced distally of said safety member distal end when said cannula is in said retracted position and said safety member is in said rest position.

45. A safety penetrating instrument for establishing a portal in the wall of an anatomical cavity comprising a housing;

an elongate cannula mounted by said housing and having a distal end for being introduced into the anatomical cavity and a proximal end for positioning externally of the anatomical cavity;

a penetrating member disposed in said cannula and having a distal end for penetrating the anatomical cavity wall;

a safety member disposed in said cannula and having a distal end, said safety member being movable relative to said housing between a safety member extended position where said safety member distal end protrudes distally from said penetrating member distal end and a safety member retracted position where said safety member distal end is disposed proximally of said penetrating member distal end to expose said penetrating member distal end;

cannula extending means for moving said cannula distally relative to said housing from a cannula retracted position where said cannula distal end is disposed proximally of said penetrating member distal end to a cannula extended position where said cannula distal end protrudes distally from said penetrating member distal end;

safety member extending means for moving said safety member distally relative to said housing from said safety member retracted position to said safety member extended position;

means for manually moving said cannula proximally relative to said housing from said cannula extended position to said cannula retracted position;

means for manually moving said safety member proximally relative to said housing from said safety member extended position to said safety member retracted position;

cannula locking means for locking said cannula in said cannula retracted position to prevent distal movement of said cannula relative to said housing beyond said cannula retracted position while permitting proximal movement of said cannula relative to said housing during penetration of the anatomical cavity wall;

safety member locking means for locking said safety member in said safety member retracted position to prevent distal movement of said safety member relative to said housing beyond said safety member retracted position while permitting proximal movement of said safety member during penetration of the anatomical cavity wall;

cannula bias means for biasing said cannula distally relative to said housing in said cannula retracted position while permitting said cannula to move proximally relative to said housing from said cannula retracted position during penetration of the anatomical cavity wall and distally toward said cannula retracted position upon introduction into the anatomical cavity;

safety member bias means for biasing said safety member distally relative to said housing in said safety member retracted position while permitting said safety member to move proximally relative to said housing from said safety member retracted position during penetration of the anatomical cavity wall and distally toward said safety member retracted position upon introduction into the anatomical cavity;

penetrating member bias means for biasing said penetrating member distally relative to said housing toward an extended rest position and for permitting said penetrating member to move proximally relative to said housing from said penetrating member rest position during penetration of the anatomical cavity wall; and releasing means responsive to penetration of said safety penetrating instrument into the anatomical cavity for triggering release of said safety member and cannula locking means to permit said safety member and cannula extending means to move said safety member and cannula distally relative to said housing from said retracted positions to said extended positions.

46. A safety penetrating instrument as recited in claim 45 wherein said safety member is a tubular safety shield disposed between said penetrating member and said cannula.

47. A safety penetrating instrument as recited in claim 45 wherein said penetrating member is at least partly hollow and said safety member is a safety probe disposed within said penetrating member.

48. A safety penetrating instrument as recited in claim 45 wherein said releasing means is responsive to distally-biased movement of said safety member upon penetrating into the anatomical cavity.

49. A safety penetrating instrument as recited in claim 45 wherein said releasing means is responsive to distally-biased movement of said penetrating member upon penetrating into the anatomical cavity.

50. A safety penetrating instrument as recited in claim 45 wherein said releasing means is responsive to distally-biased movement of said cannula upon penetrating into the anatomical cavity.

51. A safety penetrating instrument as recited in claim 45 wherein said releasing means is responsive to distally-biased movement of said safety member and said penetrating member upon penetrating into the anatomical cavity.

52. A safety penetrating instrument as recited in claim 45 wherein said releasing means is responsive to distally-biased movement of said safety member and said cannula upon penetrating into the anatomical cavity.

53. A safety penetrating instrument as recited in claim 45 wherein said releasing means is responsive to distally-biased movement of said cannula and said penetrating member upon penetrating into the anatomical cavity.

54. A safety penetrating instrument as recited in claim 45 wherein said releasing means is responsive to distally-biased movement of said safety member, said cannula and said penetrating member upon penetrating into the anatomical cavity.

55. A safety penetrating instrument as recited in claim 45 wherein said penetrating member distal end extends distally from a transverse dimensional transition in said penetrating member and said safety member distal end is aligned with said transition when in said retracted position.

56. A safety penetrating instrument as recited in claim 55 wherein said cannula distal end is aligned with said safety member distal end when said cannula is in said cannula retracted position and said safety member is in said safety member retracted position.

57. A safety penetrating instrument as recited in claim 55 wherein said cannula distal end is spaced proximally of said safety member distal end when said cannula is in said cannula retracted position and said safety member is in said safety member retracted position.

58. A safety penetrating instrument as recited in claim 55 wherein said cannula distal end is spaced distally of said safety member distal end when said cannula is in said cannula retracted position and said safety member is in said safety member retracted position.

59. A safety penetrating instrument as recited in claim 45 wherein said penetrating member distal end extends distally from a transverse dimensional transition in said penetrating member and said safety member distal end is located proximally of said transition when in said retracted position.

60. A safety penetrating instrument as recited in claim 59 wherein said cannula distal end is aligned with said safety member distal end when said cannula is in said cannula retracted position and said safety member is in said safety member retracted position.

61. A safety penetrating instrument as recited in claim 59 wherein said cannula distal end is spaced proximally of said safety member distal end when said cannula is in said cannula retracted position and said safety member is in said safety member retracted position.

62. A safety penetrating instrument as recited in claim 59 wherein said cannula distal end is spaced distally of said safety member distal end when said cannula is in said cannula retracted position and said safety member is in said safety member retracted position.

63. A safety penetrating instrument as recited in claim 45 wherein said penetrating member distal end extends distally from a transverse dimensional transition in said penetrating member and said safety member distal end is located distally of said transition when in said retracted position.

64. A safety penetrating instrument as recited in claim 63 wherein said cannula distal end is aligned with said safety member distal end when said cannula is in said cannula retracted position and said safety member is in said safety member retracted position.

65. A safety penetrating instrument as recited in claim 63 wherein said cannula distal end is spaced proximally of said safety member distal end when said cannula is in said cannula retracted position and said safety member is in said safety member retracted position.

66. A safety penetrating instrument as recited in claim 63 wherein said cannula distal end is spaced distally of said safety member distal end when said cannula is in said cannula retracted position and said safety member is in said safety member retracted position.

* * * * *